US012788773B2

(12) United States Patent
North et al.

(10) Patent No.: US 12,788,773 B2
(45) Date of Patent: Nov. 10, 2026

(54) ANTIMICROBIAL COMPOSITIONS CONTAINING POLYPHENYLENE CARBOXYMETHYLENE

(71) Applicant: Yaso Therapeutics Inc., Frisco, TX (US)

(72) Inventors: Barbara Best North, Hornbrook, CA (US); Michael Oldham, Manakin-Sabot, VA (US); Donald Paul Waller, Oak Brook, IL (US); Mary Beth Weitzel, Scottsdale, AZ (US)

(73) Assignee: Yaso Therapeutics Inc., Frisco, TX (US)

( * ) Notice: Subject to any disclaimer, the term of this patent is extended or adjusted under 35 U.S.C. 154(b) by 899 days.

(21) Appl. No.: 17/914,758

(22) PCT Filed: Mar. 24, 2021

(86) PCT No.: PCT/US2021/023932

§ 371 (c)(1),
(2) Date: Sep. 26, 2022

(87) PCT Pub. No.: WO2021/195245

PCT Pub. Date: Sep. 30, 2021

(65) Prior Publication Data

US 2024/0000828 A1 Jan. 4, 2024

Related U.S. Application Data

(60) Provisional application No. 63/071,054, filed on Aug. 27, 2020, provisional application No. 63/001,052, filed on Mar. 27, 2020.

(51) Int. Cl.
*A61K 31/765* (2006.01)
*A61P 31/06* (2006.01)

(52) U.S. Cl.
CPC ........... *A61K 31/765* (2013.01); *A61P 31/06* (2018.01)

(58) Field of Classification Search
CPC .............................. A61K 31/765; A61P 31/06
See application file for complete search history.

(56) References Cited

U.S. PATENT DOCUMENTS

| | | | | |
|---|---|---|---|---|
| 2005/0089539 | A1 | 4/2005 | Scholz et al. | |
| 2014/0371310 | A1 | 12/2014 | Anderson, Jr. et al. | |
| 2016/0199322 | A1 | 7/2016 | Myntti | |
| 2017/0143757 | A1 * | 5/2017 | Anderson, Jr ....... | A61K 31/765 |
| 2018/0055857 | A1 | 3/2018 | Kross | |

OTHER PUBLICATIONS

R. S. Subbarayan, et al. Occupational Exposure of Oropharyngeal Human Papillomavirus Amongst Otolaryngologists, Laryngoscope, Oct. 2020 ; 130(10): 2366-2371; presented at the Triological Society Annual Meeting at COSM, Austin, Texas. U.S.A, May 1-5, 2019. (Year: 2019).*

V. Kulkarni and C. Shaw. “Formulation and characterization of nasal sprays,” Inhalation, 2012, 1-5. (Year: 2012).*

L.J. Zaneveld, et al. “Use of mandelic acid condensation polymer (SAMMA), a new antimicrobial contraceptive agent, for vaginal prophylaxis,” Fertility and Sterility, vol. 78, No. 5, Nov. 2002, 1107-1115. (Year: 2002).*

Abstract of the document “Development of SAMMA based vaginal microbioside,” from the SBIR grant administered by U.S. Small Business Administration, dated 2006. (Year: 2006).*

Olivier Escaffrea, Terry L. Juelicha, Alexander N. Freiberg. “Polyphenylene carboxymethylene (PPCM) in vitro antiviral efficacy against Ebola virus in the context of a sexually transmitted infection,” Antiviral Research, vol. 170, 2019, 104567. (Year: 2019).*

Escaffre, Olivier et al.; “Polyphenylene carboxymethylene (PPCM) in vitro antiviral efficacy against Ebola virus in the context of a sexually transmitted infection”; Antiviral Research, Elsevier BV, NL, vol. 170, Jul. 24, 2019; DOI: 10.1016/J-ANTIVIRAL.2019.104567.

Mesquita, PM et al.; “Candidate Microbicide PPCM Blocks Human Immunodeficiency Virus Type 1 Infection in Cell and Tissue Cultures and Prevents Genital Herpes in a Murine Model”; Journal of Virology, vol. 82, No. 13, Jul. 1, 2008, pp. 6576-6584; doi: 10.1128/JVI.00335-08.

Herold, B.C. et al.; “Mandelic Acid Condensation Polymer: Novel Candidate Microbicide for Prevention of Human Immunodeficiency Virus and Herpes Simplex Virus Entry”; Journal of Virology, vol. 76, No. 22, Nov. 15, 2002, pp. 11236-11244; doi: 10.1128/JVI.76.22.11236-11244.2002.

Escaffre, Olivier et al.; “Polyphenylene Carboxymethylene (PPCM) In Vitro antiviral efficacy against Ebola virus in the context of a sexually transmitted infection”; Antiviral Research; Oct. 2019; 22 pages.

* cited by examiner

*Primary Examiner* — Michael P Cohen
(74) *Attorney, Agent, or Firm* — Jackson Walker LLP

(57) ABSTRACT

In an embodiment, the present disclosure pertains to a method to minimize infectivity and replication of an infection or reduce inflammation caused by the infection. Generally, the method includes administering a composition to a subject, where the composition includes a condensation polymer. In some embodiments, the method further includes at least one of binding, by the position, to a site on a virus, bacteria or fungi associated with the infection to thereby inhibit replication of the virus, bacteria, or fungi and reducing, by the composition, inflammation related to the infection. In another embodiment, the present disclosure pertains to a method to minimize infectivity and replication of a pathogen. Generally, the method includes applying a composition to clothing, where the composition includes a condensation polymer.

6 Claims, 12 Drawing Sheets

ANTIMICROBIAL COMPOSITIONS CONTAINING POLYPHENYLENE CARBOXYMETHYLENE

CROSS-REFERENCE TO RELATED APPLICATIONS

This patent application claims priority from, and incorporates by reference the entire disclosure of, U.S. Provisional Patent Application No. 63/001,052 filed on Mar. 27, 2020 and U.S. Provisional Patent Application No. 63/071,054 filed on Aug. 27, 2020.

TECHNICAL FIELD

The present disclosure relates generally to antimicrobial (e.g., antibacterial, antifungal, and antiviral) compositions and more particularly, but not by way of limitation, to antimicrobial compositions containing polyphenylene carboxymethylene.

BACKGROUND

This section provides background information to facilitate a better understanding of the various aspects of the disclosure. It should be understood that the statements in this section of this document are to be read in this light, and not as admissions of prior art.

Airborne diseases include any infections that are caused via transmission through the air. Airborne pathogens transmitted may be any kind of microbe, and they may be spread in aerosols, dust, liquids, bodily fluids (e.g., saliva or mucus), on surfaces, and the like. As used herein, the term "microbe" refers to any type of bacteria, fungus, virus, or pathogen, and the term "antimicrobial" refers to any antibacterial, antifungal, antiviral, or other anti-pathogen agents, components, compositions, mechanisms, and the like. Recently, airborne pathogens such as, but not limited to, viral and bacterial infections have become an increasing problem in light of their highly contagious nature. The aforementioned types of infections are of major concern globally, especially in view of the worldwide outbreak of severe acute respiratory syndrome coronavirus 2 (SARS-CoV-2). While many people wear personal protective equipment (PPE) to protect against airborne pathogens, PPE is not a failsafe measure. The present disclosure seeks to remedy the defects associated with PPE-only use by providing for compositions to minimize, reduce, or inhibit infectivity and replication of an infection or reduce infection-related inflammation caused by airborne pathogens. Various embodiments of the present disclosure relate to both external application/administration (e.g., on PPE or hair) and internal application/administration (e.g., in the nasal cavity or in the lungs).

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure pertains to a method to minimize infectivity and replication of an infection or reduce inflammation caused by the infection. Generally, the method includes administering a composition to a subject, where the composition includes a condensation polymer. In some embodiments, the method further includes at least one of binding, by the composition, to a site on a virus, bacteria, or fungi associated with the infection to thereby inhibit replication of the virus, bacteria, or fungi, and reducing, by the composition, inflammation related to the infection.

In some embodiments, the condensation polymer is a mandelic acid condensation polymer. In some embodiments, the mandelic acid condensation polymer is polyphenylene carboxymethylene (PPCM). In some embodiments, the PPCM has a sulfur content less than 0.1 wt. %.

In some embodiments, the administering is a mechanism that includes, without limitation, nasal administration, nasal spray administration, eye administration, eye drop administration, inhalation administration, nebulizer administration, dry powder inhaler administration, metered dose inhaler administration, aerosol administration, topical administration, and combinations thereof. In some embodiments, the administering includes internal administration to the subject. In some embodiments, the administering includes distributing the composition to an internal region of the subject including, without limitation, an eye, a lung, a tracheobronchial airway, a pulmonary airway, a nasal passage, a throat, a trachea, an extrathoracic airway, a respiratory tract, pharyngeal areas, laryngeal airways, oral, vaginal, and combinations thereof. In some embodiments, the administering includes external administration to at least one of the subject and clothing to be worn by the subject. In some embodiments, the clothing to be worn by the subject is personal protective equipment. In some embodiments, the personal protective equipment includes, without limitation, gloves, masks, gowns, aprons, scrubs, pant covers, arm covers, face covers, hair covers, beard covers, leg covers, shoes, and combinations thereof. In some embodiments, the administering includes at least one of spraying the composition on to the clothing to be worn by the subject, soaking the clothing to be worn by the subject in a solution including the composition, rubbing the composition on the clothing to be worn by the subject, and combinations thereof. In some embodiments, the administering includes distributing the composition to an external region of the subject including, without limitation, skin, hair, and combinations thereof.

In some embodiments, the composition has an average molecular weight of less than about 10,000 Daltons. In some embodiments, the composition further includes excipients. In some embodiments, the composition is in a form including, without limitation, an aqueous solution, a gel, a lotion, a cream, an aerosol, an ocular aqueous solution, a nasal aqueous solution, and combinations thereof.

In some embodiments, the infection is caused by an airborne pathogen. In some embodiments, the infection includes, without limitation, a viral infection, a bacterial infection, and combinations thereof. In some embodiments, the infection is a viral infection from a viral family including, without limitation, Adenoviridae, Picornaviridae, Togaviridae, Orthomyxoviridae, Paramyxoviridae, Filoviridae, Coronavirus, Herpesviridae, Papillomaviridae, and combinations thereof. In some embodiments, the infection is a viral infection including, without limitation, adenoviruses, rhinovirus, poliovirus, rubella virus, influenza A, influenza B, influenza C, measles, mumps, respiratory syncytial infection (RSI), Ebola virus, coronavirus, severe acute respiratory syndrome (SARS), and Coronavirus disease 2019 (COVID-19), Smallpox, Yellow Fever, Dengue Fever, West Nile Viruses, Zika Virus, Hepatitis C, Hepatitis B, Herpes Simplex Virus (HSV-1 and HSV-2), Human Papillomavirus (HPV), sexually transmitted diseases, and combinations thereof. Newly discovered viruses not classified in the above-mentioned groups are also envisioned.

In some embodiments, the infection is a bacterial infection from bacteria including, but not limited to, *Bordetella pertussis, Mycoplasma pneumoniae, Chlamydia pneumoniae, Klebsiella pneumoniae, Haemophilus influenzae, Pseudomonas aeruginosa, Pseudomonas pseudomallei, Actinomyces israelii, Legionella parisiensis, Legionella pneumophila, Cardiobacterium, Alkaligenes, Yersinia pestis, Pseudomonas cepacia, Pseudomonas maillei, Enterobacter cloacae, Enterococcus, Neisseria meningitidis, Streptococcus faecalis, Streptococcus pyogenes, Mycobacterium kansasii, Mycobacterium tuberculosis, Streptococcus pneumoniae, Staphylococcus aureus, Staphylococcus epidermis, Corynebacteria diphtheria, Clostridium tetani, Haemophilus parainfluenzae, Moraxella lacunata, Bacillus anthracis, Mycobacterium avium, Mycobacterium intracellulare, Acinetobacter, Moraxella catarrhalis, Serratia marcescens, Saccharomonospora viridis, Neisseria gonorrhoeae, Treponema pallidum*, and combinations thereof. Newly discovered bacteria not classifiable to the above-mentioned groups are also envisioned. In some embodiments, the infection is a bacterial infection including, without limitation, whooping cough, pneumonia, bronchitis, meningitis, actinomycosis, pneumonia, Legionnaires' disease, pontiac fever, opportunistic infections, pneumonic plague, non-respiratory infections, meningitis, scarlet fever, pharyngitis, cavitary pulmonary, tuberculosis, pneumonia, otitis media, diptheria, anthrax, opportunistic infections, farmer's lung, gonorrhea, syphilis, sexually transmitted diseases, and combinations thereof. In some embodiments, the composition is in a topical form and the administering includes topical application of the composition on the subject.

In another embodiment, the present disclosure pertains to a method to minimize infectivity and replication of a pathogen. Generally, the method includes applying a composition to clothing, where the composition includes a condensation polymer. In some embodiments, the method further includes binding, by the composition, to a site on a virus, bacteria, or fungi associated with the pathogen to thereby inhibit replication of the virus, bacteria, or fungi. In some embodiments, the clothing is personal protective equipment. In some embodiments, the personal protective equipment includes, without limitation, gloves, masks, gowns, aprons, scrubs, pant covers, arm covers, face covers, hair covers, beard covers, leg covers, shoes, and combinations thereof. In some embodiments, the applying includes at least one of spraying the composition on to the clothing, soaking the clothing in a solution including the composition, rubbing the composition on the clothing, and combinations thereof. In some embodiments, the condensation polymer is a mandelic acid condensation polymer. In some embodiments, the mandelic acid condensation polymer is polyphenylene carboxymethylene (PPCM).

BRIEF DESCRIPTION OF THE DRAWINGS

A more complete understanding of the subject matter of the present disclosure may be obtained by reference to the following Detailed Description when taken in conjunction with the accompanying Drawings wherein:

FIG. 14A shows values indicate the percentage of IAV infectivity compared to samples incubated with vehicle alone (medium only). Results show the average of quadruplicate data points. Data were adjusted to a sigmoid function and IC50 values were calculated using GraphPad Prism software fitting a normalized dose-response curve with a variable slope. IC50 values are summarized in Table 3. FIG. 14B shows values indicate the percent viability as compared to samples incubated with vehicle alone (medium only). Results show the average of quadruplicate data points. Data were adjusted to a sigmoid function and CC50 values were calculated using GraphPad Prism software fitting a dose-response curve with a variable slope (four parameters). When viability did not reach 50%, the CC50 value reported was greater than 1,250 μg/mL. CC50 values are indicated in Table 3.

DETAILED DESCRIPTION

Figure 1:
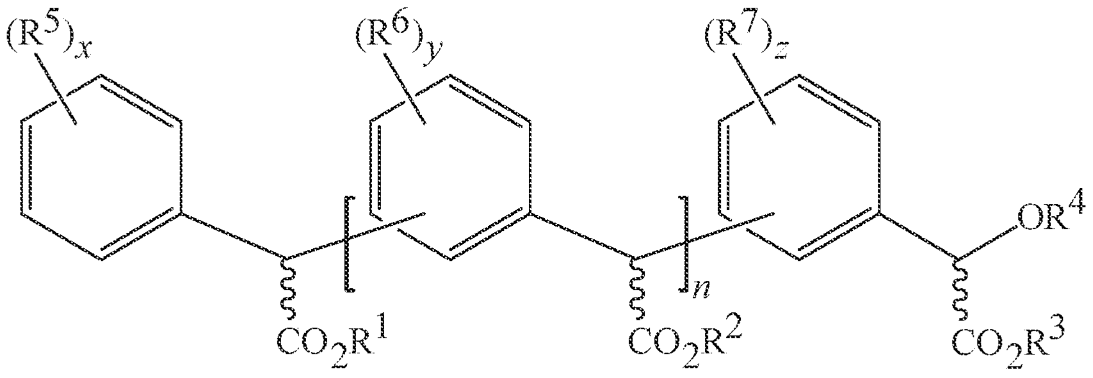
FIG. 1 illustrates a generic structure of a broadly acting condensation polymer of mandelic acid.

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

The present disclosure seeks to address the problem of infections transmitted either through direct contact with bodily fluids, body parts, surfaces, inhalation of nasal droplets expressed by sneezing, coughing, talking, laughing, yelling, air borne dust containing viruses or other pathogens, air borne pathogens, and combinations of the same and like. The aforementioned types of infections are of major concern globally, especially in view of the worldwide outbreak of severe acute respiratory syndrome coronavirus 2 (SARS-CoV-2). While many in certain professions wear personal protective equipment (PPE) to protect against pathogens, such as, for example, surgeons and medical first responders, PPE is not failsafe. As such, an aspect of the present disclosure seeks to provide compositions that are applied topically to various areas inside and outside of the body, including, but not limited, to the skin, eyes, and nose, where such compounds would enhance the use of PPE. Professions that would benefit from these products include, but are not limited to, surgeons, border patrol, caregivers of elderly, the sick and disabled, clinical lab personnel, custodians/sanitization teams, emergency department personnel, farm workers, medical laboratory researchers, nurses, outpatient care providers (e.g., dialysis and radiology providers), paramedics/emergency responders, physicians, phlebotomists, reference laboratory personnel, public health workers, school teachers, specimen couriers, and others persons who come in close contact with potentially infected persons. Furthermore, aspects of the present disclosure are directed towards compositions, such as the aforementioned, to offer protection to individuals who do not normally wear PPE, but have the potential to be at risk of infection.

In various aspects, the present disclosure relates generally to compositions having a broadly acting condensation polymer of mandelic acid, polyphenylene carboxymethylene (PPCM), that is capable of being applied internally and externally via various administration modes (e.g., inhalation or lotions). The novel concept of utilizing PPCM internally and externally has led to surprising results demonstrating superiority to typical hand sanitizers, which are generally used by both those who use PPE and those that do not use PPE. For example, hand sanitizers only work briefly after application, hand sanitizers cannot be utilized internally (e.g., application in the eyes and nose), and hand sanitizers kill all bacteria, including beneficial bacteria. Additionally, as disclosed herein, PPCM can be applied prior to exposure and is active at the moment of contact with a pathogen. This feature is not possible with current hand sanitizers or hand washing procedures. Furthermore, the active polymer disclosed herein (e.g., PPCM) is safe and can be applied as a skin lotion, as an ocular aqueous solution, a nasal aqueous solution, and combinations of the same and like.

Reference will now be made to more specific embodiments of the present disclosure and data that provide support for such embodiments. However, it should be noted that the disclosure below is for illustrative purposes only and is not intended to limit the scope of the claimed subject matter in any way.

The small polymer PPCM, depicted in FIG. 1 as a generic structure of a broadly acting condensation polymer of mandelic acid, has been shown to be active against a broad range of viruses and bacteria through a primary method of attachment and fusion inhibition. PPCM demonstrates activity against viral infection by preventing the attachment and fusion of virus to host cell attachments sites. For instance, PPCM binds to glycoprotein B-2 (gpB-2) on the herpes virus, which prevents herpes attachment and fusion. Additionally, PPCM prevents cell-to-cell transmission and primary infection by multiple clades of the human immunodeficiency virus 1 (HIV-1) by binding gp120. Both the herpes virus and HIV are from different viral families, and both viruses can be transmitted by direct contact. The Ebola virus, a deadly filovirus which can be transmitted through direct contact, sneezing, and sexual intercourse, is also inhibited by PPCM in a dose-dependent manner Table 1, shown below, illustrates viral infection examples from various virus families in which the compositions of the present disclosure can inhibit activity against. In addition, Table 1 illustrates how the viral infections are spread.

TABLE 1

| Family | Infection Example | Sexual Transmission | Airborne |
|---|---|---|---|
| Adenoviridae | Adenoviruses | No | Yes |
| Picornaviridae | Rhinovirus and Poliovirus | No | Yes |
| Togaviridae | Rubella Virus | No | Yes |
| Orthomyxoviridae | Influenza (A, B, C) | No | Yes |
| Paramyxoviridae | Measles, Mumps, and Respiratory Syncytial Infection (RSI) | No | Yes |
| Filoviridae | Ebola Virus | Yes | Yes |
| Coronavirus | Coronavirus, Severe Acute Respiratory Syndrome (SARS), and Coronavirus Disease 2019 (COVID-19) | No | Yes |
| Poxviridae | Smallpox | | |
| Flaviviridae | Yellow Fever, Dengue Fever, West Nile Viruses, Zika Virus, and Hepatitis C | Some | No |
| Hepadnaviridae | Hepatitis B | Yes | No |
| Herpesviridae | Herpes Simplex Virus (HSV-1 and HSV-2) | Yes | No |
| Papillomaviridae | Human Papillomavirus (HPV) | Yes | No |

Table 2, shown below, illustrates bacterial infection examples from various bacterial strains in which the compositions of the present disclosure can inhibit activity against. In addition, Table 2 illustrates potential points of contacts for contraction of the bacterial infections.

TABLE 2

| Bacteria | Infection Example | Contraction | |
|---|---|---|---|
| *Bordetella pertussis* | Whooping Cough | Contagious | Humans |
| *Mycoplasma pneumoniae* | Pneumonia | Contagious | Humans |
| *Chlamydia pneumoniae* | Pneumonia and Bronchitis | Contagious | Humans |
| *Klebsiella pneumoniae* | Opportunistic Infections | Endogenous | Environmental |
| *Haemophilus influenzae* | Meningitis | Contagious | Humans |
| *Pseudomonas aeruginosa* | Opportunistic Infections | Contagious | Environmental |
| *Pseudomonas pseudomallei* | Opportunistic Infections | Non | Environmental |
| *Actinomyces israelii* | Actinomycosis | Endogenous | Humans |
| *Legionella parisiensis* | Pneumonia | Non | Environmental |
| *Legionella pneumophila* | Legionnaires' Disease and Pontiac Fever | Non | Environmental |
| *Cardiobacterium* | Opportunistic Infections | Endogenous | Humans |
| *Alkaligenes* | Opportunistic Infections | Endogenous | Humans |
| *Yersinia pestis* | Pneumonic Plague | Contagious | Rodents |
| *Pseudomonas cepacia* | Non-Respiratory | Non | Environment |
| *Pseudomonas mallei* | Opportunistic Infections | Non | Environment |
| *Enterobacter cloacae* | Non-Respiratory | Contagious | Humans |
| *Enterococcus* | Non-Respiratory | Contagious | Humans |
| *Neisseria meningitidis* | Meningitis | Endogenous | Humans |
| *Streptococcus faecalis* | Non-Respiratory | Contagious | Humans |
| *Streptococcus pyogenes* | Scarlet Fever, Pharyngitis | Contagious | Humans |
| *Mycobacterium kansasii* | Cavitary Pulmonary | Non | Unknown |
| *Mycobacterium tuberculosis* | Tuberculosis | Contagious | Humans |
| *Streptococcus pneumoniae* | Pneumonia and Otitis Media | Contagious | Humans |
| *Staphylococcus aureus* | Opportunistic Infections | Endogenous | Humans |
| *Staphylococcus epidermis* | Non-Respiratory | Endogenous | Humans |
| *Corynebacteria diphtheria* | Diptheria | Contagious | Humans |

TABLE 2-continued

| Bacteria | Infection Example | Contraction | |
|---|---|---|---|
| *Clostridium tetani* | Non-Respiratory | Non | Environment |
| *Haemophilus parainfluenzae* | Opportunistic Infections | Endogenous | Humans |
| *Moraxella lacunata* | Opportunistic Infections | Endogenous | Humans |
| *Bacillus anthracis* | Anthrax | Non | Cattle |
| *Mycobacterium avium* | Cavitary Pulmonary | Non | Environment |
| *Mycobacterium intracellulare* | Cavitary Pulmonary | Non | Environment |
| *Acinetobacter* | Opportunistic Infections | Endogenous | Environment |
| *Moraxella catarrhalis* | Opportunistic Infections | Endogenous | Humans |
| *Serratia marcescens* | Opportunistic Infections | Endogenous | Environment |
| *Saccharomonospora viridis* | Farmer's Lung | Non | Agricultural |
| *Neisseria gonorrhoeae* | Gonorrhea | Contagious | Humans |
| *Treponema pallidum* | Syphilis | Contagious | Humans |

Full-Dose Antiviral Testing on PPCM Na Salt ("Test-Item"). Assay against live SARS-CoV-2 was performed against the MEX-BC2/2020 strain, which contains the D614G mutation in the spike protein. Assay against influenza was performed against the A/California/07/2009 (H1N1) strain. The test-item (PPCM Na salt) was provided as 10 mg/mL stocks and was kept at room temperature until use. The test-item was assessed in parallel for antiviral and viability assays.

The testing utilized two adherent cell lines to evaluate the antiviral activity of the test-items against different viruses. In brief, test-items were either pre-incubated with the target cells (live SARS-CoV-2 assay), and for the testing against influenza A virus (IAV), the putative inhibitors were pre-incubated with virus for 30 min before adding the virus and inhibitor mix to the cells. Inhibitors were present in the cell culture medium for the duration of the infection as described below. For each antiviral assay, a viability test was set up in parallel using the same concentrations of inhibitors tested in the antiviral assays. Viability assays were used to determine compound-induced cytotoxicity effects in the absence of virus. Cell viability was determined by the neutral red (NR) uptake method (SARS-CoV-2) or by the XTT method (IAV). Viability assays were conducted for the same periods of time evaluated in the corresponding antiviral assays.

Eight dilutions of the sample were tested in triplicates or quadruplicates for the antiviral and viability assays (SARS-CoV-2 and IAV, respectively). Three-fold serial dilutions started at 1,250 µg/mL. When possible, half-maximal inhibitory concentration (IC50; antiviral) and 50% cytotoxic concentration (CC50; inhibition of viability) values of the test-items were determined using GraphPad Prism software.

SARS-CoV-2. For this test, Vero E6 cells were utilized to evaluate the antiviral activity of the test-items against SARS-CoV-2. Test-items were pre-incubated first with target cells for 1 hour at 37° C., before infection with SARS-CoV-2. Following pre-incubation, cells were challenged with viral inoculum. Putative inhibitors were present in the cell culture for the duration of the infection (96 hours), at which time a neutral red uptake assay was performed to determine the extent of the virus-induced cytopathic effect (CPE). Prevention of the virus-induced CPE was used as a surrogate marker to determine the antiviral activity of the test-items against SARS-CoV-2. Controls wells were also included with known inhibitors of SARS-CoV-2: GS-441524 (a metabolite of remdesivir), the main plasma metabolite of the polymerase inhibitor remdesivir (GS-5734), and chloroquine diphosphate (CQ), a broad antiviral with activity against coronaviruses.

IAV. For the influenza assay, A549 cells were utilized to evaluate the antiviral activity of the test-items against A/California/07/2009. Test-items were pre-incubated with the virus for 30 minutes before adding the virus and inhibitor mix to the cells. Test-items were present in the cell culture medium for the duration of the infection. Cells were challenged with virus in the presence of different concentrations of test-item or the control baloxavir (BLX) (inhibitor of the cap-dependent endonuclease activity of the influenza polymerase). The extent of infection was monitored after 2 days of infection, by quantifying the levels of viral antigens with a colorimetric readout. Antiviral activity against this virus was evaluated with an immunoassay to monitor expression of viral antigens in cells infected with the virus.

SARS-CoV-2 Antiviral Assay. To evaluate antiviral activity against SARS-CoV-2 the isolate MEX-BC2/2020 carrying a D614G mutation in the viral spike protein was used. A CPE-based antiviral assay was performed by infecting Vero E6 cells in the presence or absence of test-items. Infection of cells leads to significant cytopathic effect and cell death after 4 days of infection. In this assay, reduction of CPE in the presence of inhibitors was used as a surrogate marker to determine the antiviral activity of the tested items. Viability assays to determine test-item-induced loss of cell viability was monitored in parallel using the same readout (neutral red), but utilizing uninfected cells incubated with the test-items.

Vero E6 cells were maintained in Dulbecco's Modified Eagle Medium (DMEM) with 10% fetal bovine serum (FBS), herein referred to as DMEM10. Twenty-four hours after cell seeding, test samples were submitted to serial dilutions with DMEN with 2% FBS (DMEM2) in a different plate. Then, media was removed from cells, and serial dilutions of test-items were added to the cells and incubated for 1 hour at 37° C. in a humidified incubator. After cells were pre-incubated with test-items, then cultures were challenged with SARS-CoV-2 resuspended in DMEM2. The amount of viral inoculum was previously titrated to result in a linear response inhibited by antivirals with known activity against SARS-CoV-2. Cell culture media with the virus inoculum was not removed after virus adsorption, and test-items and virus were maintained in the media for the duration of the assay (96 hours). After this period, the extent of cell viability was monitored with the neutral red uptake assay.

Figure 2:
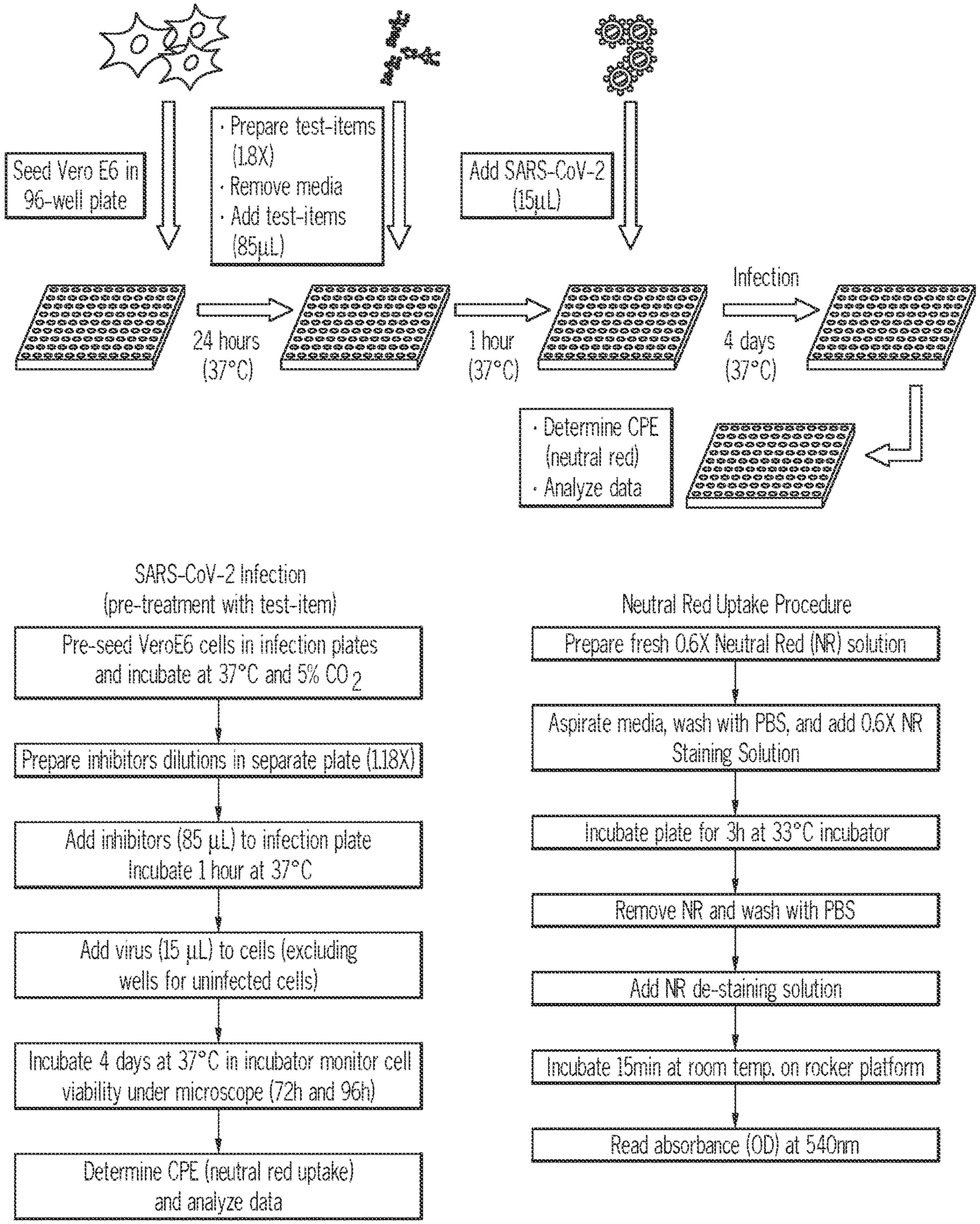
FIG. 2 illustrates an experimental outline to evaluate SARS-CoV-2 (MEX-BC2/2020) induced cytopathic effect (CPE). The top shows a diagram and the bottom shows a flow chart. Vero E6 cells are seeded 24 hours prior to infection, and then dilutions of PPCM Na salt ("test-items") were added and allowed to incubate for 1 hour. Following incubation, virus was added and infections were allowed for 96 hours before monitoring CPE with the neutral red (NR) uptake method.

The virus-induced CPE was monitored under the microscope after 3 days of infection. After 4 days, cells were stained with neutral red to monitor cell viability. Viable cells incorporate neutral red in their lysosomes. The uptake of neutral red relies on the ability of live cells to maintain the pH inside the lysosomes lower than in the cytoplasm, a process that requires ATP. Inside the lysosome, the dye becomes charged and is retained. After a 3 hour incubation with neutral red (0.033%), the extra dye is washed away, and the neutral red is extracted from lysosomes by incubating cells for 15 minutes with a solution containing 50% ethanol and 1% acetic acid. The amount of neutral red is estimated by measuring absorbance at 540 nm in a plate reader. The procedure followed to determine the anti-SARS-CoV-2 activity of test-items is summarized in FIG. 2.

Test-items were evaluated in triplicates using serial 3-fold dilutions. Controls included uninfected cells ("mock-infected"), and infected cells to which only vehicle was added. Some cells were also treated with chloroquine (CQ) at 5 μM. CQ is an immunosuppressant and anti-malarial drug with broad antiviral activity against coronaviruses. Some cells were treated with GS-441524 (1 μM and 10 μM). GS-441524 is the main metabolite of remdesivir, a broad-spectrum antiviral that blocks the RNA polymerase of SARS-CoV-2.

Data Analysis of CPE-Based Antiviral Assay. The average absorbance at 540 nm (A540) observed in infected cells (in the presence of vehicle alone) was calculated, and then subtracted from all samples to determine the inhibition of the virus induced CPE. Data points were then normalized to the average A540 signal observed in uninfected cells ("mock") after subtraction of the absorbance signal observed in infected cells. In the neutral red CPE-based assay, uninfected cells remained viable and uptake the dye at higher levels than non-viable cells. In the absence of antiviral agents the virus-induced CPE kills infected cells and leads to lower A540 (this value equals 0% inhibition). By contrast, incubation with the antiviral agents (GS-441524) prevents the virus induced CPE and leads to absorbance levels similar to those observed in uninfected cells. Full recovery of cell viability in infected cells represent 100% inhibition of virus replication.

Influenza Antiviral Assay. To determine antiviral activity against influenza virus type A/California/07/2009 an immunostaining assay was used to monitor the extent of infection. In this type of assay, infected cells are fixed and then a cocktail of anti-influenza antibodies is used to quantify the amount of viral antigen using a colorimetric readout.

Figure 3:
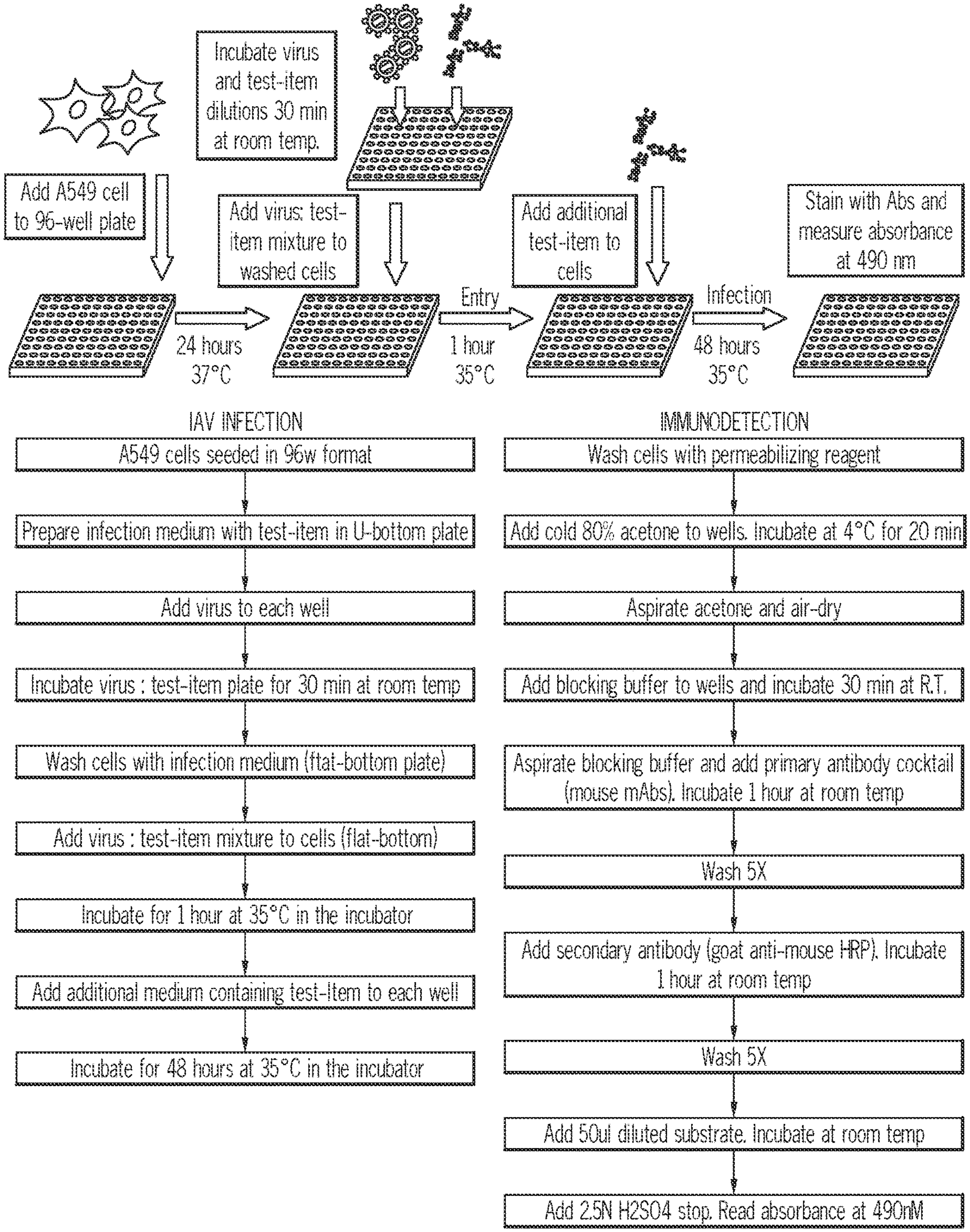
FIG. 3 illustrates an experimental outline of the influenza replication assay. A549 cells are seeded 24 hours prior to infection. Then, pre-incubated mixtures of influenza A and test-items are added to the cells for 1 hour at 35° C. to allow viral entry. After this incubation, additional test-item is added to the infection plate and the infection is allowed for 48 more hours. After that period, cells are fixed, stained with a cocktail of mouse monoclonal antibodies, and the amount of viral antigen present is revealed with a colorimetric reaction. Absorbance at 490 nm is monitored to determine the level of influenza antigens present in the cells.

IAV Infectivity Assay. The A/CA/07/2009 strain was used to infect A549 cells (human lung carcinoma cells). Cells were maintained in DMEM with 10% fetal bovine serum (FBS), herein referred to as DMEM10. The day before infection, cells were seeded at 15,000 cells per well in a 96-well clear flat bottom plate and incubated at 37° C. for 24 hours. The day of infection, test-items were three-fold serially diluted or five-fold for control inhibitor, in U-bottom plates using OptiMEM with 0.3% bovine serum albumin (BSA) and 2 μg/mL TPCK trypsin, herein referred to as infection medium. Dilutions were prepared at 2× the final concentration. Equal volumes of A/California/07/2009 virus diluted in infection medium and 2× concentrated test-item or control inhibitor were incubated for 30 minutes at room temperature. The volume of virus used in the assay was previously determined to produce a signal in the linear range inhibited by baloxavir, a cap-dependent endonuclease inhibitor of the influenza polymerase. Following the 30-minute pre-incubation, cells were washed with infection medium, then 50 μL of the virus/test-item mixture was added to the cells and the plate was incubated at 35° C. in a humidified incubator with 5% $CO_2$ for 1 hour. After allowing viral entry, an additional 50 μL of the corresponding test-item or control inhibitor in infection medium was added to each well. The final volume was 100 μL of 1× concentrated samples. All dilutions for test-items, control inhibitors, mock, and vehicle samples were diluted in infection medium. The cells were incubated at 35° C. in the incubator (5% $CO_2$) for 48 hours. The procedure followed in the IAV antiviral assay is summarized in FIG. 3.

Test-item was evaluated in four replicates using serial 3-fold dilutions in influenza infection medium. Controls included cells incubated with no virus ("mock-infected"), infected cells incubated with infection medium (vehicle control), with infection medium containing vehicle 12.5% phosphate-buffered saline (PBS), and with 0.2 μM baloxavir (positive control). A full dose-response inhibition curve (single data points) with baloxavir (5-fold serial dilutions ranging from 0.01 nM to 1 μM) was also assessed. After 48 hours of infection, cells were stained with an immunostaining protocol using a cocktail of 4 different anti-influenza antibodies to quantify infection levels.

QC and Analysis of IAV Assay Data. Infectivity was determined by monitoring the absorbance at 490 nm. All data points were calculated as a percentage of the average signal observed in the vehicle controls from infected cells treated with infection medium alone. The signal-to-background (S/B) for this assay was 3.3 (determined as the percentage of infection cells treated with infection medium only compared to that of "mock-infected" cells). Baloxavir decreased the amount of viral antigen in infected cells with IC50 values of 0.49 nM. The average variation for all replicate data points was 5.5 (average of all coefficients of variation (C.V.) values). The average variation for all data points displaying greater than 50% infection was 7.0% (C.V.>50% infection).

Cytotoxicity Assays: Viability Assay (Neutral Red Uptake Method or XTT Method) to Assess Test-Item-Induced Cytotoxicity. Uninfected cells were incubated with test-item or control inhibitor dilutions using the same experimental setup and inhibitor concentrations used in the corresponding infectivity assays. The incubation temperature and duration of the incubation period mirrored the conditions of the corresponding infectivity assay.

For the SARS-CoV-2 assay, cell viability was evaluated with the neutral red uptake method utilizing uninfected cells. The extent of viability was monitored by measuring absorbance at 540 nm. When analyzing the data, background levels obtained from wells with no cells were subtracted from all data-points. Absorbance readout values were given as a percentage of the average signal observed in uninfected cells treated with vehicle alone.

For the IAV cytotoxicity assay, cell viability was evaluated with the XTT method. The tetrazolium salt (XTT) is cleaved to an orange formazan dye throughout a reaction that occurs only in viable cells with active mitochondria. The formazan dye is directly quantified using a scanning multi-well spectrophotometer. Background levels obtained from wells with no cells were subtracted from all data-points. The extent of viability was monitored by measuring absorbance at 490 nm.

QC and Analysis of Cytotoxicity Data. For the SARS-CoV-2 cytotoxicity assay, the average signal obtained in wells with no cells was subtracted from all samples. Readout values were given as a percentage of the average signal observed in uninfected cells treated with vehicle alone (DMEM2). The signal-to-background (S/B) obtained was 20.8-fold. Dimethyl sulfoxide (DMSO) was used as a cytotoxic compound control in the viability assays. DMSO blocked cell viability by more than 99% when tested at 10% (Table 3).

For the IAV cytotoxicity assay, the average signal obtained in wells with no cells was subtracted from all samples. Readout values were given as a percentage of the average signal observed in uninfected cells treated with vehicle alone (infection medium alone). The signal-to-background (S/B) obtained was 11.2. Emetine was used as a cytotoxic compound control in the viability assay and inhibited cell viability greater than 85% at 10 μM.

Figure 4A:
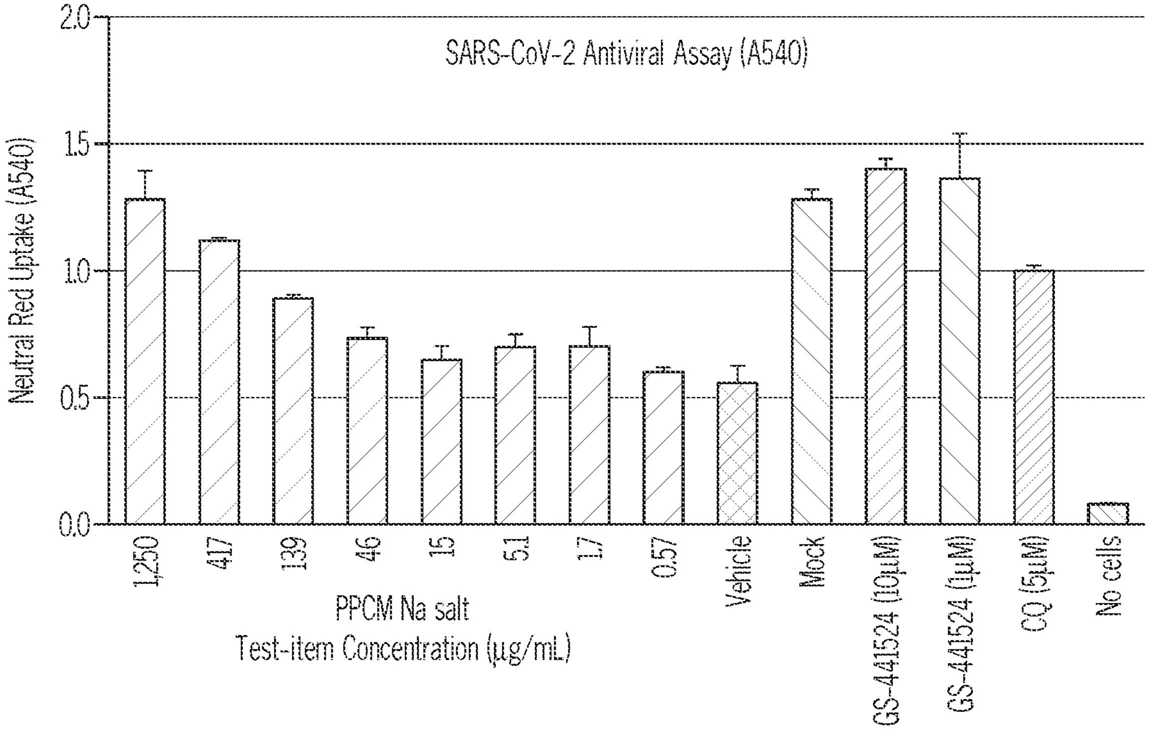
FIG. 4A and FIG. 4B illustrate inhibition by test-items of SARS-CoV-2-induced CPE (A540) (FIG. 4A) and the dose-response observed with GS-441524, a metabolite of remdesivir (single data-points) (FIG. 4B). Cell viability was monitored to determine the virus induced-CPE. Data are shown as raw A540 values in wells containing Vero E6 cells infected in the presence of either vehicle alone or varying concentrations of test-items (average of triplicates with standard deviation). Uninfected cells are shown as "Mock". Background levels are shown in wells without cells ("no cells"). GS-441524 at 1 μM and 10 μM and chloroquine diphosphate (CQ) at 5 μM are included as positive controls.
Figure 5A:
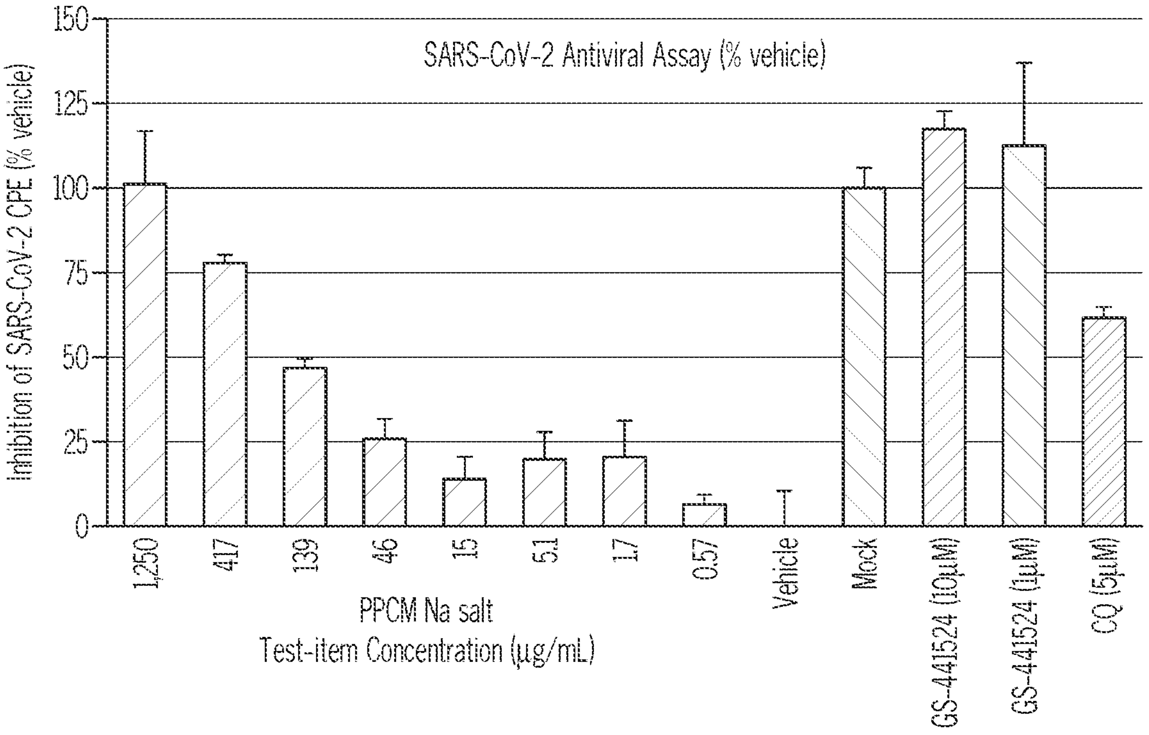
FIG. 5A and FIG. 5B illustrate inhibition by test-items of the CPE mediated by SARS-CoV-2 (percentage values) (FIG. 5A) and the dose-response observed with GS-441524 (FIG. 5B). Values show the inhibition of the SARS-CoV-2 induced CPE, as a surrogate marker for virus replication. Data were analyzed as shown in Table 5, with values normalized to the A540 values observed in uninfected cells after subtraction of the average absorbance observed in infected cells in the presence of vehicle. Values in uninfected cells ("mock") are included for comparison (100% inhibition). Data plotted for test-items shows the average and standard deviation of triplicates. GS-441524 at 1 μM and 10 μM, and CQ at 5 μM are included as positive controls.
Figure 6A:
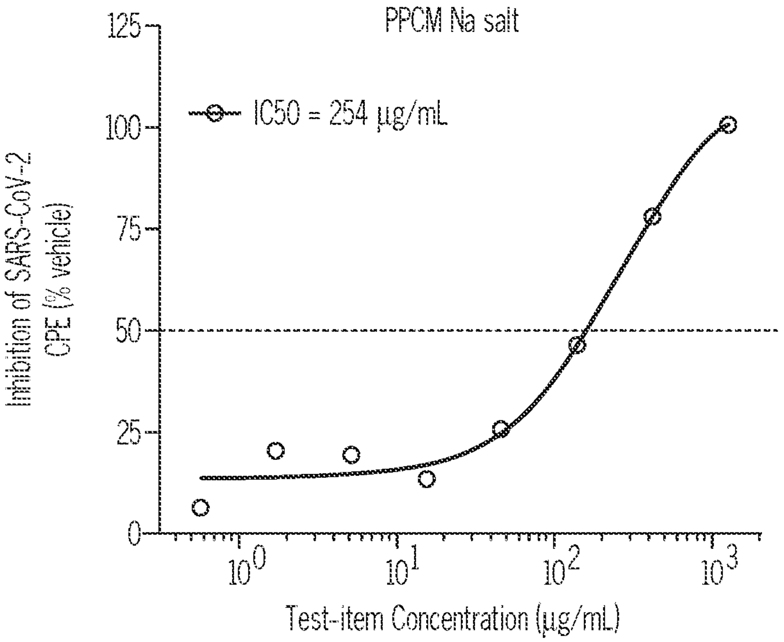
FIG. 6A and FIG. 6B illustrate half-maximal inhibitory concentration (IC50) values for inhibition of SARS-CoV-2 CPE by test-items (FIG. 6A) and GS-441524 (FIG. 6B). Values indicate the percentage inhibition of the CPE induced by live SARS-CoV-2 (MEX-BC2/2020), as compared to samples incubated with no test-item (vehicle alone). Results show the average of triplicates data points for test-item or single data points for GS-441524. When possible, data were modeled to a sigmoidal function using GraphPad Prism software fitting a dose-response curve with a variable slope (four parameters). IC50 values are also summarized in Table 3.

Results: Antiviral Activity of PPCM Na Salt (Test-Item) Against SARS-CoV-2. PPCM Na salt completely prevented the virus-induced cytopathic effect (CPE) at the highest concentration tested (1,250 μg/mL). The protective effect was observed in a dose-dependent manner starting at the lowest concentration evaluated (FIG. 4A, FIG. 5A, and FIG. 6A).

Figure 7:
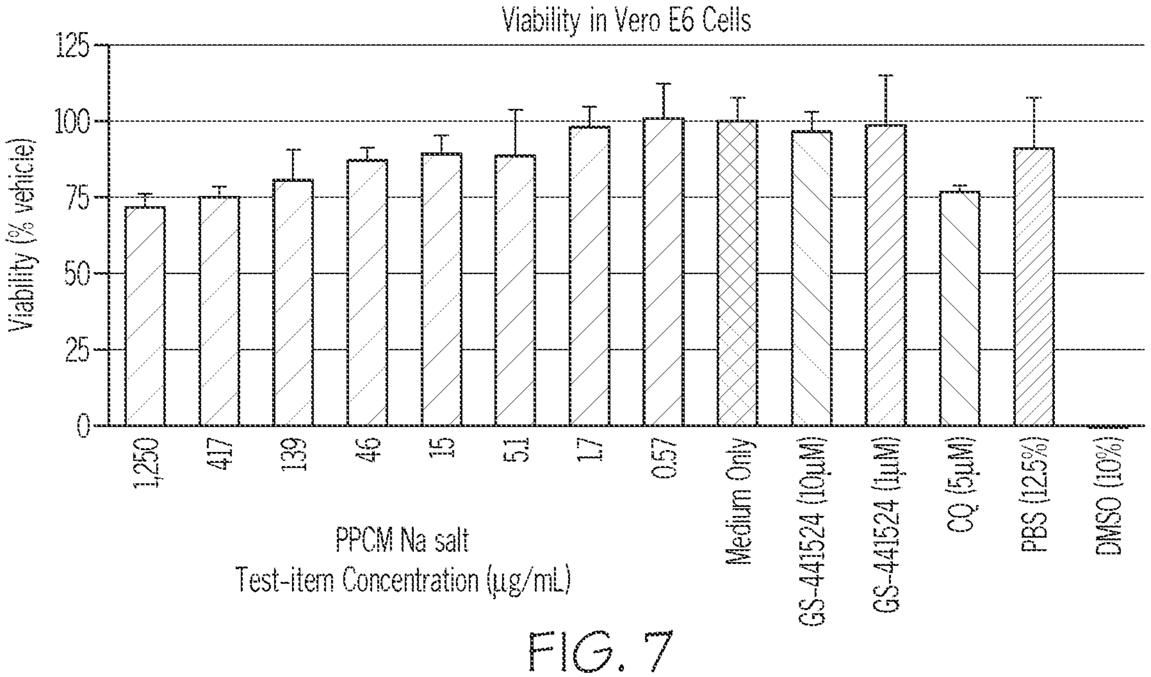
FIG. 7 illustrates viability in uninfected Vero E6 cells (percentage values). Results show the extent of cell viability as determined by the neutral red uptake assay (A540) after 4 days. Data are normalized to the values observed in cells in the absence of test-items ("vehicle", medium only). Results show the average of triplicate data points with the standard deviation (s.d.). Average and standard deviation values for cells treated with vehicle (medium only) are derived from six replicates.

These findings suggest that PPCM Na salt inhibits the replication of SARS-CoV-2 in infected cells. The cytotoxicity displayed by the test-item at concentrations above 15 μg/mL (FIG. 7) may have partially reduced the antiviral effect seen at the highest concentrations tested. Microscopic evaluation of the monolayers after 96 hours of infection confirmed the prevention of the virus-induced CPE exerted by PPCM Na salt.

Figure 8:
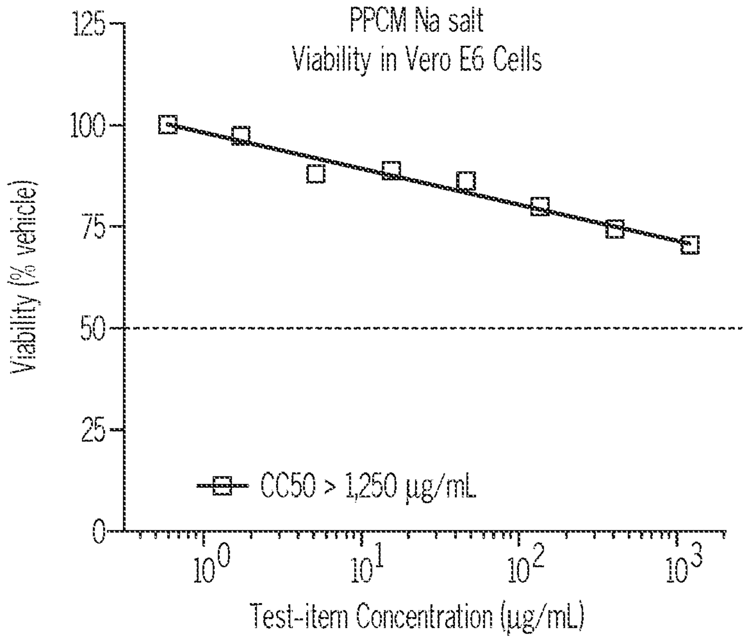
FIG. 8 illustrates 50% cytotoxic concentration (CC50) values for Vero E6 cell viability in the presence of test-items (percentage values). Values indicate the percent viability estimated as percentage of that observed in samples incubated with vehicle (medium only). Results show the average of triplicate data points. Data were adjusted to a sigmoid function when possible, and CC50 values were calculated using GraphPad Prism software fitting a dose-response curve with a variable slope (four parameters). CC50 values are also summarized in Table 3.

FIG. 8 illustrates CC50 values for Vero E6 cell viability in the presence of test-items (percentage values). Values indicate the percent viability estimated as percentage of that observed in samples incubated with vehicle (medium only). Results show the average of triplicate data points. Data were adjusted to a sigmoid function when possible, and CC50 values were calculated using GraphPad Prism software fitting a dose-response curve with a variable slope (four parameters). CC50 values are also summarized in Table 3, shown below.

Figure 4B:
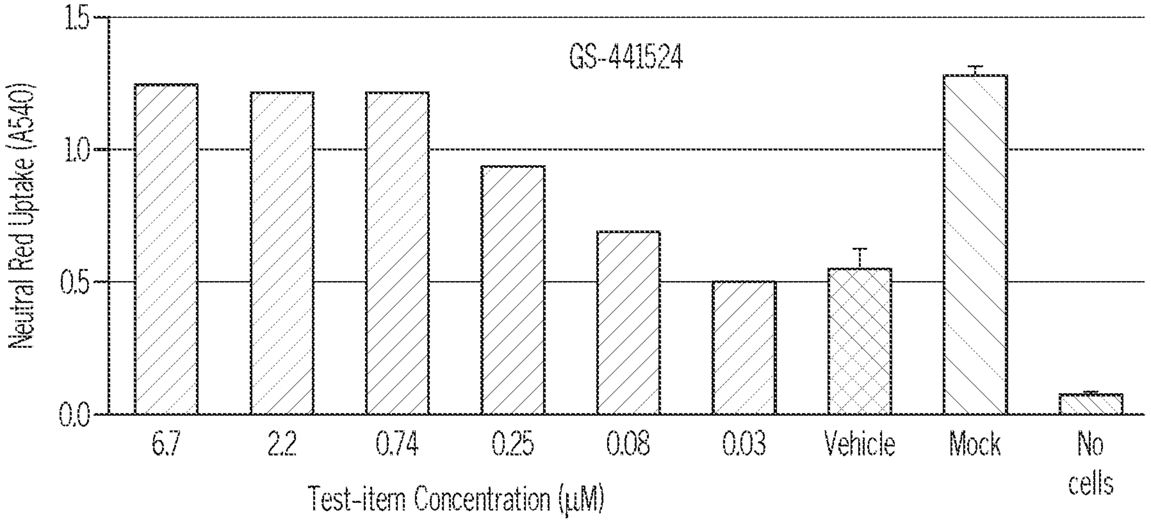
Figure 5B:
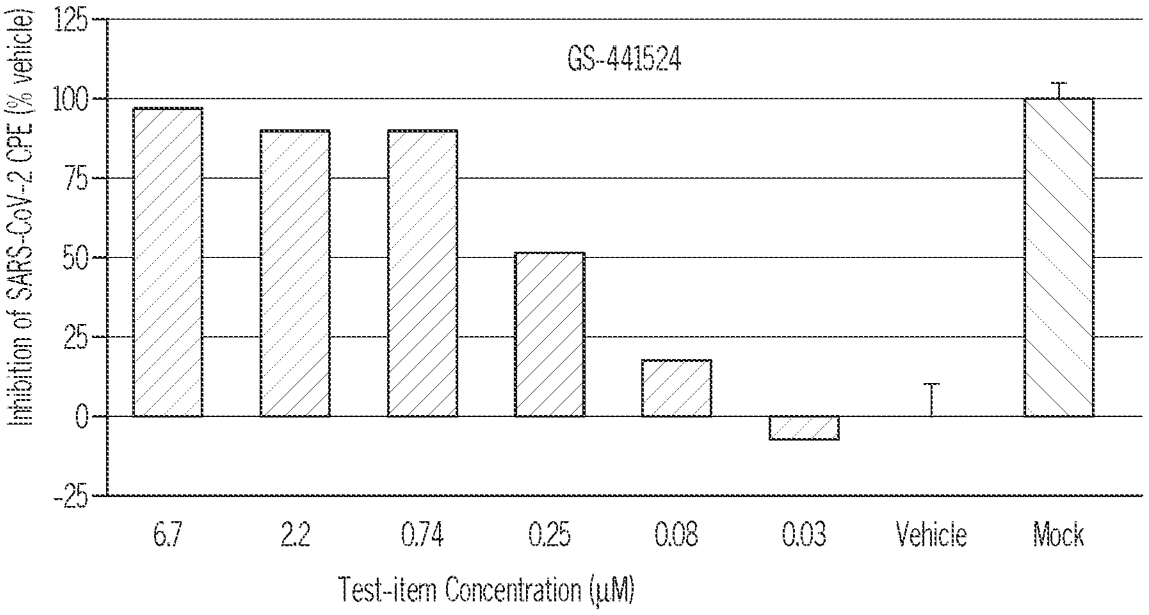
Figure 6B:
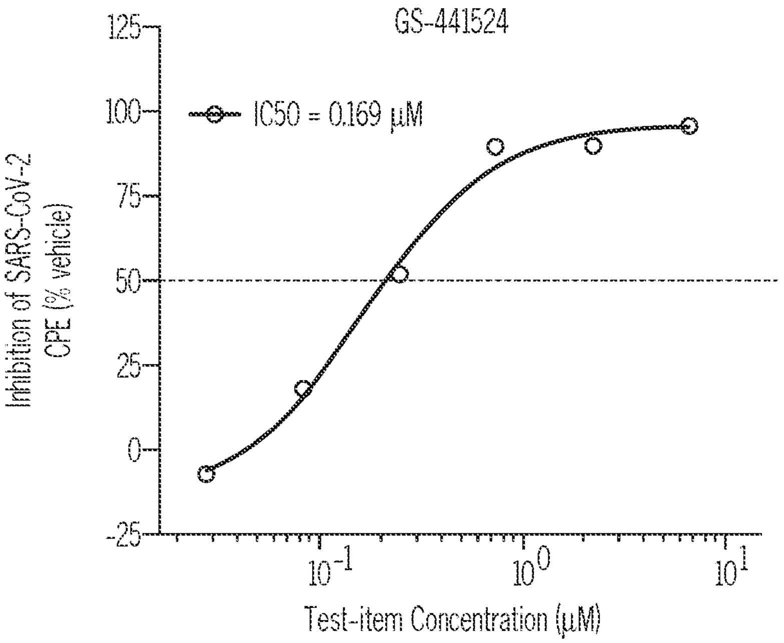

By comparison, the control inhibitor GS-441524 at concentrations of 1 μM, completely prevented the virus-induced CPE (FIG. 4B, FIG. 5B, and FIG. 6B). Microscopic evaluation of the monolayers also confirmed the prevention of the virus-induced CPE exerted by GS-441524.

Figure 9A:
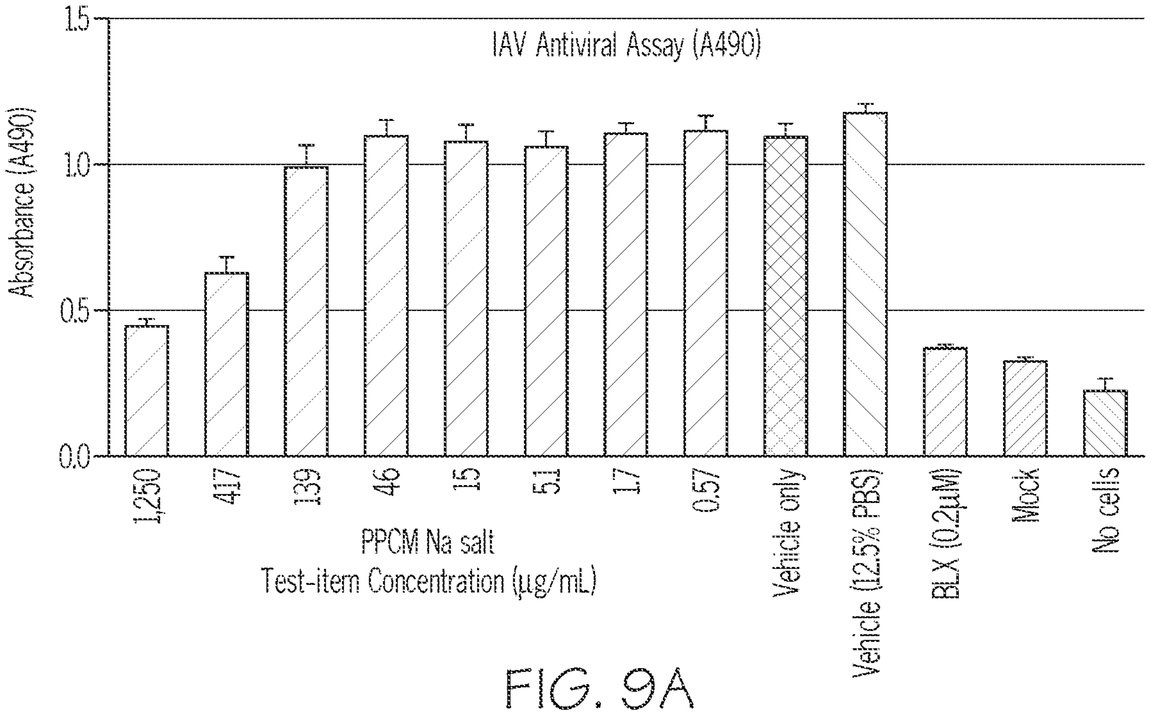
FIG. 9A and FIG. 9B illustrate inhibition by test-items of Influenza A Virus (IAV; A490) (FIG. 9A) and the dose-response observed with baloxavir (single data-points) (FIG. 9B). Data are shown as A490 values in wells containing A549 cells infected in the presence of either vehicle alone or varying concentrations of test-items (average of quadruplicates with standard deviation). Uninfected cells are shown as "Mock". Background levels are shown in wells without cells ("no cells"). baloxavir (BLX) at 0.2 μM and vehicle 12.5% phosphate-buffered saline (PBS) are included as controls.
Figure 9B:
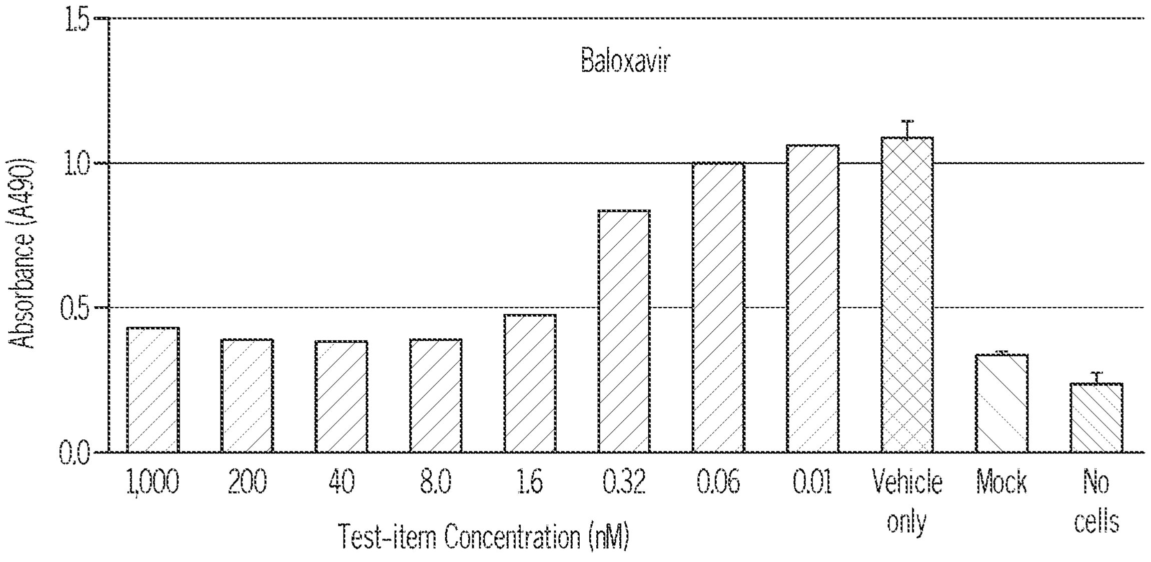
Figure 10A:
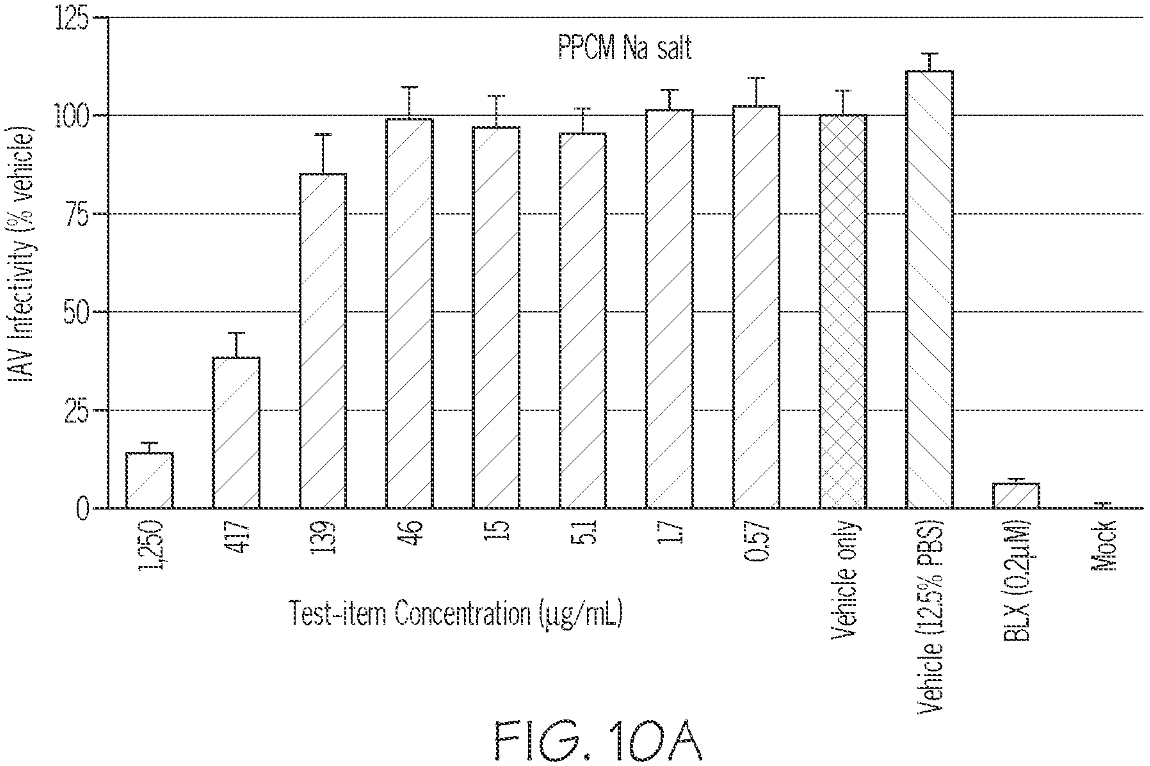
FIG. 10A and FIG. 10B illustrate inhibition of IAV infectivity by test-items (percentage values) (FIG. 10A) and the dose-response observed with the control antiviral, baloxavir (FIG. 10B). Results show the extent of IAV infection, as determined by an immunostaining readout for infectivity at 48 hours. Data are normalized to the activity observed in cells in the absence of test-item (vehicle alone). Results show the average of quadruplicate data points with the standard deviation (s.d.) for test-item.
Figure 11A:
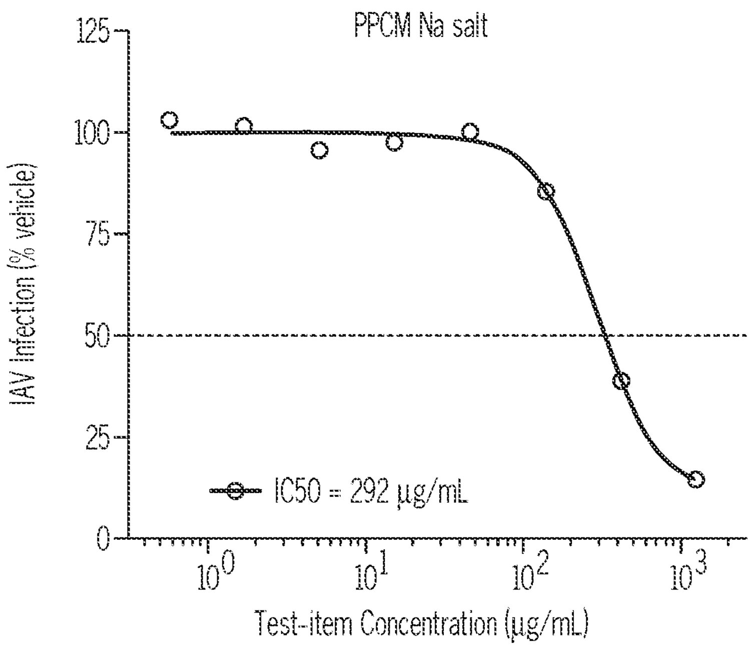
FIG. 11A and FIG. 11B illustrate IC50 values for inhibition of IAV infectivity by test-item (FIG. 11A) and control antiviral (percentage values) (FIG. 11B). Results show the extent of IAV infection, as determined by an immunostaining readout for infectivity. Values indicate the percentage of IAV infectivity compared to samples incubated with vehicle alone (medium only). Results show the average of quadruplicate data points for test item or single data points for baloxavir. When possible, data were adjusted to a sigmoid function and IC50 values were calculated using GraphPad Prism software fitting a dose-response curve with a variable slope (four parameters). IC50 values are summarized in Table 3.
Figure 12:
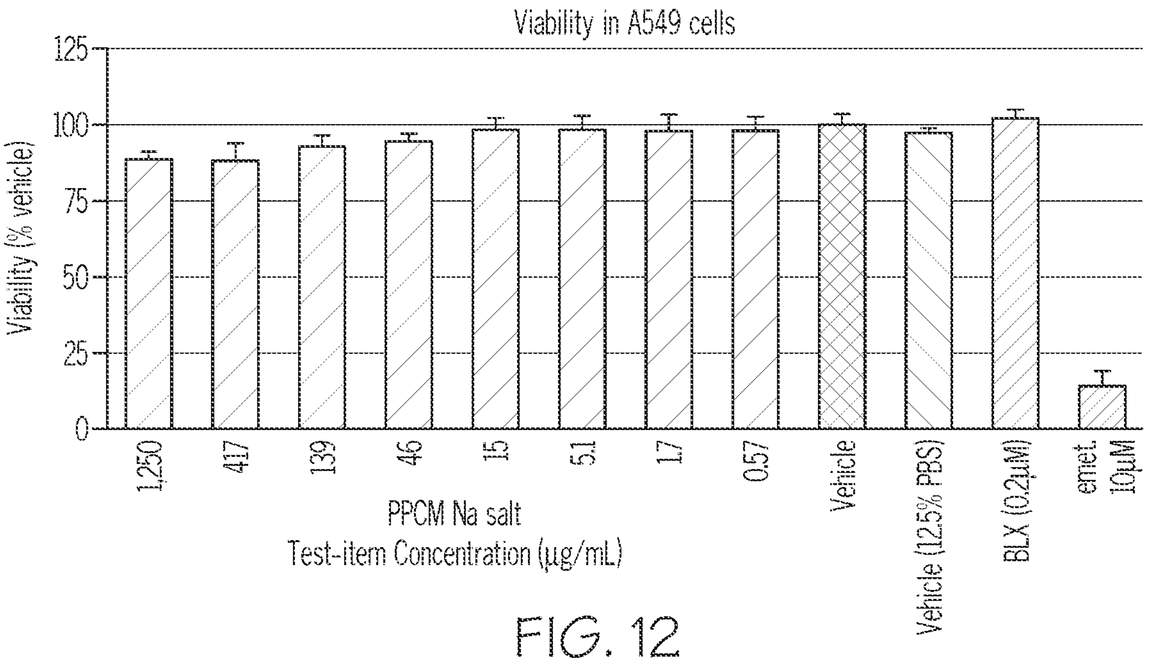
FIG. 12 illustrates viability in uninfected A549 cells (percentage values). Results show the extent of compound-induced cytotoxicity in A549 cells incubated for 48 hours, as determined by an XTT readout for viability (absorbance 490 nm readout). Data were normalized to the values observed in cells in the absence of test-item vehicle alone (medium only). Results show the average of quadruplicate data points with the standard deviation for test-item.
Figure 13:
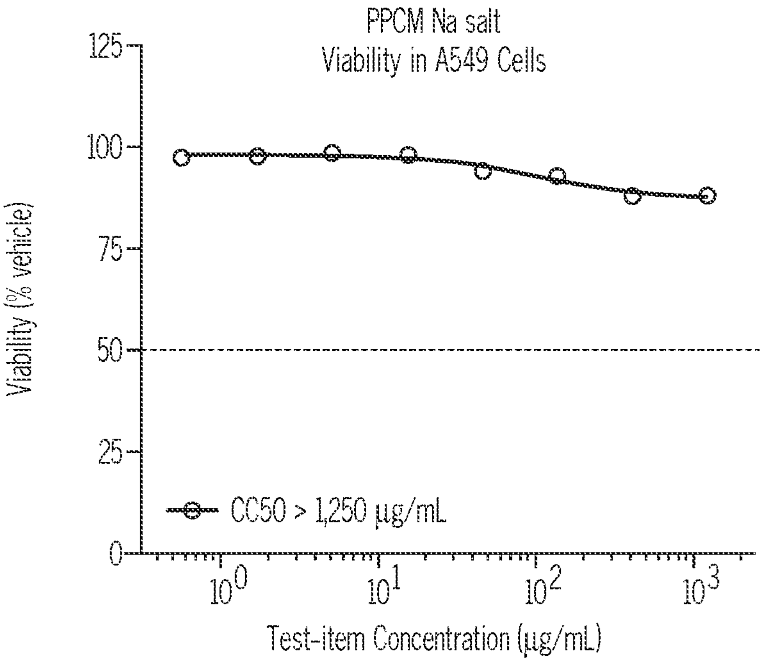
FIG. 13 illustrates CC50 values for A549 cell viability in the presence of test-item (percentage values). Results show the extent of compound-induced cytotoxicity in A549 cells incubated for 48 hours, as determined by an XTT readout for viability (absorbance 490 nm readout). Values indicate the percent viability estimated as percentage of that observed in samples incubated with vehicle alone (medium only). Results show the average of quadruplicate data points. Data were adjusted to a sigmoid function and CC50 values were calculated using GraphPad Prism software fitting a dose-response curve with a variable slope (four parameters). When viability did not reach 50%, the CC50 value reported was greater than 1,250 μg/mL. CC50 values are indicated in Table 3.

Results: Antiviral Activity of PPCM Na Salt against Influenza A/California/07/2009 Strain. FIG. 9A and FIG. 9B illustrate inhibition by test-items of IAV (A490) (FIG. 9A) and the dose-response observed with baloxavir (single data-points) (FIG. 9B). Data are shown as A490 values in wells containing A549 cells infected in the presence of either vehicle alone or varying concentrations of test-items (average of quadruplicates with standard deviation). Uninfected cells are shown as "Mock". Background levels are shown in wells without cells ("no cells"). BLX at 0.2 μM and vehicle 12.5% PBS are included as controls. PPCM Na salt displayed antiviral activity against influenza A/California/07/2009 virus strain at doses at or above 139 μg/mL (FIG. 10A and FIG. 11A). Some loss of viability was observed in the viability assays with uninfected cells (FIG. 12 and FIG. 13).

Figure 10B:
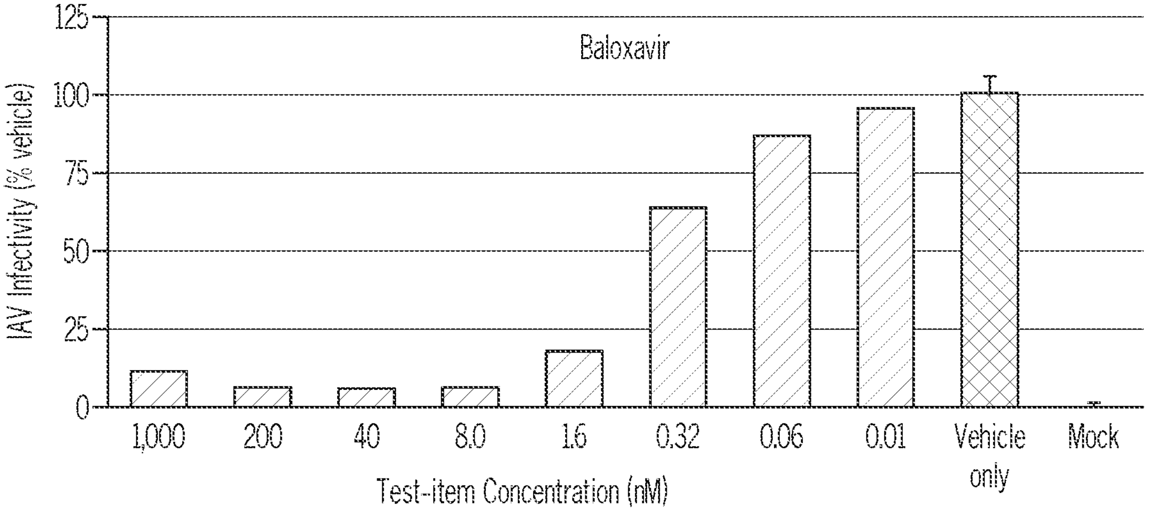
Figure 11B:
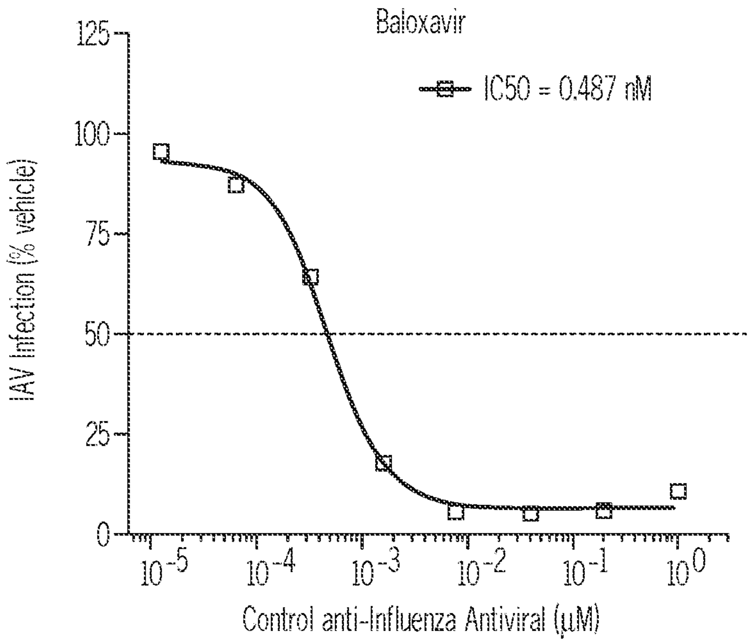

When tested in parallel, baloxavir (BLX), an inhibitor of the cap-dependent endonuclease activity of the influenza polymerase, potently blocked replication of influenza at concentrations in the low nanomolar range. The IC50 value generated for BLX was 0.49 nM (FIG. 10B and FIG. 11B).

Figure 14A:
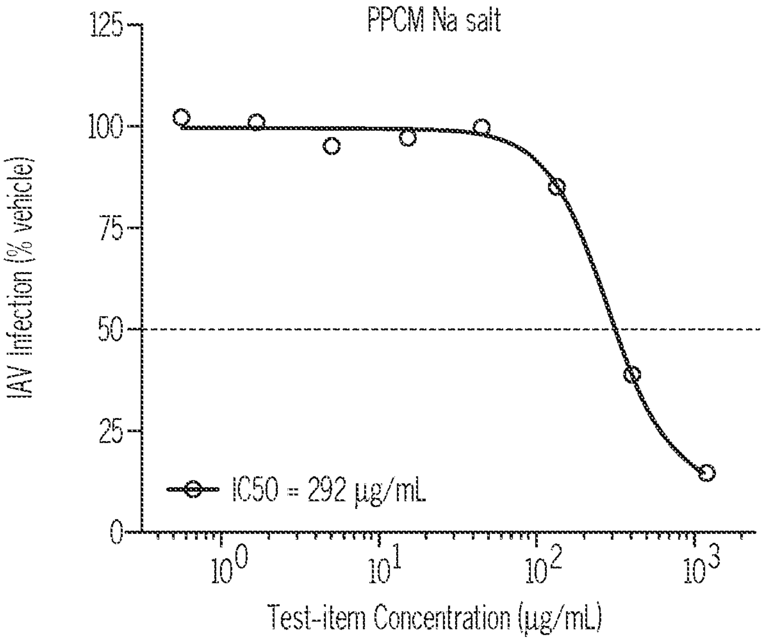
FIG. 14A and FIG. 14B illustrate a comparison of the anti-IAV activity and compound-induced toxicity of test-item in A549 cells.
Figure 14B:
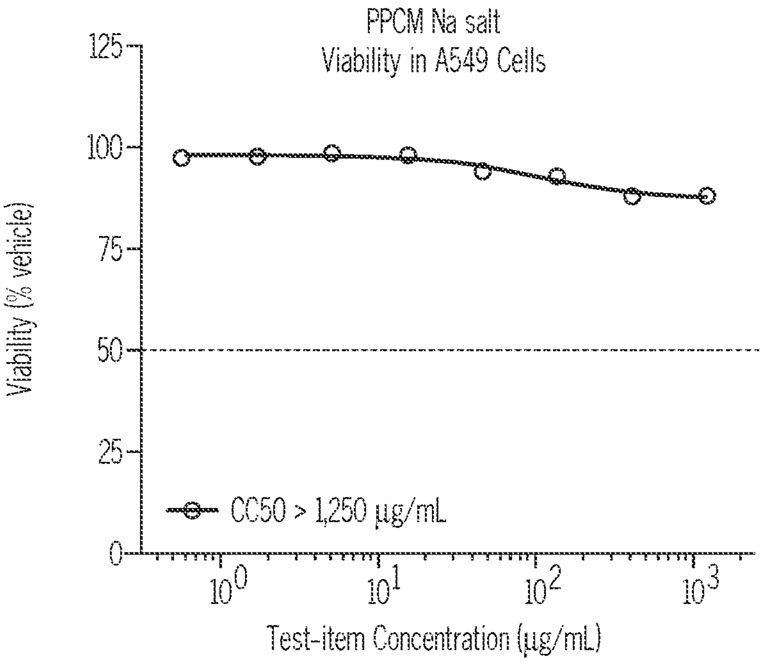

FIG. 14A and FIG. 14B illustrate comparison of the anti-IAV activity and compound-induced toxicity of test-item in A549 cells. FIG. 14A shows values indicate the percentage of IAV infectivity compared to samples incubated with vehicle alone (medium only). Results show the average of quadruplicate data points. Data were adjusted to a sigmoid function and IC50 values were calculated using GraphPad Prism software fitting a normalized dose-response curve with a variable slope. IC50 values are summarized in Table 3, shown below. FIG. 14B shows values indicate the percent viability as compared to samples incubated with vehicle alone (medium only). Results show the average of quadruplicate data points. Data were adjusted to a sigmoid function and CC50 values were calculated using GraphPad Prism software fitting a dose-response curve with a variable slope (four parameters). When viability did not reach 50%, the CC50 value reported was greater than 1,250 μg/mL. CC50 values are indicated in Table 3.

Control Inhibitors and Quality Controls. Quality controls for the infectivity assays were performed on every plate to determine: i) signal to background (S/B) values; ii) inhibition by known inhibitors of SARS-CoV-2 or IAV (for antiviral assays); and iii) variation of the assay, as measured by the coefficient of variation (C.V.) of all data points.

All controls worked as anticipated for each assay. GS-441524, a known inhibitor of SARS-CoV-2 infection, prevented completely the virus-induced CPE of the infected cells. The IC50 obtained for GS-441524 was 0.17 μM, with no significant loss of viability in uninfected cells observed at 10 μM. Baloxavir, a known antiviral for influenza infection, blocked infection over 99% at some concentrations tested, and when assessed in full dose response curve it blocked viral replication as reported in literature (IC50 0.49 nM).

For SARS-CoV-2 assay, the overall variation of triplicates in the antiviral assay was 6.2% (Table 3), and overall variation in the viability assays was 7.3%. The ratio of signal-to-background (S/B) for the antiviral assay was 2.3-fold, determined by comparing the A540 nm values in uninfected ("mock") cells with that observed in cells challenged with SARS-CoV-2 in the presence of vehicle alone. When comparing the signal in uninfected cells to the signal in "no-cells" background wells, the S/B ratio of the antiviral assay was 16.7-fold. For the viability assay, the signal to background ("no cells" value) was 20.8-fold.

For the IAV assay, the overall variation in the infection assay was 5.5%. The overall variation for all quadruplicates in the viability assay was 6.2%. The S/B in the infection assay was 3.3, and 11.2 in the viability assay.

Table 3, illustrated below, shows the summary of results. IC50 (antiviral), and CC50 (cytotoxicity) values are shown for the test-item (in μg/mL), and for the known antivirals GS-441524 (SARS-CoV-2) or baloxavir (influenza) for each assay. Signal-to-background ratios (S/B), average coefficients of variation (C.V.), and selectivity index (S.I.) are shown. The average C.V. was determined for all replicate data-points in the CPE assay (antiviral), or the viability assay (cytotoxicity with uninfected cells). When viral inhibition or cell viability did not reach 50% at the highest concentration tested, the IC50 or CC50 values are shown as greater than the highest concentration tested.

TABLE 3

| Sample | Live SARS-CoV-2 Antiviral Assay IC50 (μg/mL) | S/B[1] | C.V.[2] | Cytotoxicity Assay (Vero E6 Cells) CC50 (μg/mL) | S/B[1] | C.V.[2] | S.I.[3] |
|---|---|---|---|---|---|---|---|
| PPCM Na Salt | 254 | 2.3 | 6.2% | >1,250 | 20.8 | 7.3% | >4.9 |
| GS-441524 (Control) | 0.17 μM | 2.3 | 6.2% | n.t. | n.t. | n.t | n.d. |

| Sample | IAV Antiviral Assay IC50 (μg/mL) | S/B[4] | C.V.[2] | Cytotoxicity Assay (A549 Cells) CC50 (μg/mL) | S/B[4] | C.V.[2] | S.I.[3] |
|---|---|---|---|---|---|---|---|
| PPCM Na Salt | 292 | 3.3 | 5.5 | >1,250 | 11.2 | 6.2 | >4.3 |
| Baloxavir (Control) | 0.49 nM | 3.3 | 5.5 | n.t. | n.t. | n.t | n.d. |

[1]Signal to background in the SARS-CoV-2 antiviral assay was calculated by dividing the signal in uninfected cells ("mock-infected"), by the signal in infected cells. Signal to background level for cytotoxicity was calculated by dividing the signal in cells in the presence of vehicle alone (medium only), divided by the signal in wells with no cells ("no cells").

[2]C.V. for the antiviral assays were calculated as the average of C.V. values determined for all replicate data points.

[3]The selectivity index is calculated by dividing the CC50 value by the IC50 value

[4]Signal to background in the influenza antiviral assay was calculated by dividing the signal in cells infected in the presence of vehicle alone, divided by the signal in uninfected cells ("mock-infected"). Signal to background level for cytotoxicity was calculated by dividing the signal in cells in the presence of vehicle alone (medium only), divided by the signal in wells with no cells ("no cells").

n.d.: not determined n.t. not tested

Table 4, shown below, illustrates protection from SARS-CoV-2-induced CPE by test-items (A540). Raw values represent A540 levels obtained determining the uptake of neutral red into viable cells. Infected cells develop CPE after four days of infection and displayed significantly reduced absorbance levels. Triplicates A540 values are shown for each test-item concentration. All samples were infected except those indicated as "mock". Samples treated with GS-441524 (1 μM and 10 μM) and CQ (5 μM) are also shown. Varying concentrations of GS-441524 were also evaluated. Test-item concentrations are shown in μg/mL and GS-441524 in μM.

infected cells in the presence of vehicle alone are indicative of no inhibition of the virus-induced CPE. Complete inhibition (100%) results in A540 levels equal to those observed in mock-infected cells (with vehicle alone). To obtain percentage inhibition values, the average A540 in cells infected in the absence of test-items ("vehicle", see Table 4) was subtracted from all values, and then these values were normalized to those obtained for uninfected cells ("mock"). Uninfected cells in the presence of vehicle alone are equal to 100% inhibition. Percentage inhibition is shown for each test condition. All samples shown below were infected except those indicated as "mock". Some samples are treated

TABLE 4

Absorbance (540 nm)

| | Conc. (μg/mL) 1,250 | 417 | 139 | 46 | 15 | 5.1 | 1.7 | 0.57 | Vehicle | Mock | GS-441524 (10 μM) | GS-441524 (1 μM) | CQ (5 μM) | No cells |
|---|---|---|---|---|---|---|---|---|---|---|---|---|---|---|
| PPCM Na Salt | 1.359 | 1.102 | 0.901 | 0.771 | 0.592 | 0.715 | 0.651 | 0.587 | 0.466 | 1.217 | 1.427 | 1.239 | 1.011 | 0.074 |
| | 1.330 | 1.128 | 0.892 | 0.692 | 0.662 | 0.733 | 0.787 | 0.619 | 0.631 | 1.293 | 1.372 | 1.489 | 0.985 | 0.079 |
| | 1.151 | 1.114 | 0.865 | 0.746 | 0.687 | 0.625 | 0.654 | 0.583 | 0.586 | 1.255 | | | | |

| | Conc. (μM) 6.7 | 2.2 | 0.74 | 0.25 | 0.08 | 0.03 | 0.604 | 1.285 |
|---|---|---|---|---|---|---|---|---|
| GS-441524 | 1.248 | 1.202 | 1.200 | 0.926 | 0.682 | 0.499 | 0.564 | 1.330 |
| | | | | | | | 0.449 | 1.270 |

Table 5, shown below, illustrates SARS-CoV-2 CPE assay (percentage values). Data below show the inhibition of the SARS-CoV-2 (MEX-BC2/2020) induced CPE in Vero E6 cells. Prevention of the virus induced CPE was used as a surrogate marker to determine the extent of replication of SARS-CoV-2. The lower levels of neutral red uptake in with GS-441524 or CQ, known antiviral agents with activity against SARS-CoV-2. Test-item concentrations are shown in micrograms per mL and controls in micromolar. Data shown for test-item represent the average and standard deviation of triplicates. For uninfected cells ("mock") and "vehicle", the standard deviation was derived from six replicates.

TABLE 5

| Inhibition of SARS-CoV-2 (MEX-BC2/2020) Virus-Induced CPE (%) | | | | | | | | |
|---|---|---|---|---|---|---|---|---|
| | Conc. (μg/mL) | | | | | | | |
| | 1,250 | 417 | 139 | 46 | 15 | 5.1 | 1.7 | 0.57 |
| PPCM Na Salt | 100.7 ± 15.5 | 77.9 ± 1.8 | 46.3 ± 2.6 | 25.7 ± 5.6 | 13.4 ± 6.8 | 19.4 ± 8.0 | 20.3 ± 10.7 | 6.4 ± 2.7 |
| | Conc. (μM) | | | | | | | |
| | 6.7 | 2.2 | 0.74 | 0.25 | 0.08 | 0.03 | | |
| GS-441524 | 96.3 | 89.9 | 89.7 | 51.9 | 18.2 | −7.0 | | |

| Inhibition of SARS-CoV-2 (MEX-BC2/2020) Virus-Induced CPE (%) | |
|---|---|
| Vehicle | 0.0 ± 10.4 |
| Mock | 100.0 ± 5.2 |
| GS-441524 (10 μM) | 117.2 ± 5.4 |
| GS-441524 (1 μM) | 112.3 ± 24.4 |
| CQ (5 μM) | 61.8 ± 2.5 |

Table 6, shown below, illustrates viability of Vero E6 cells in the presence of test-item as determined by the neutral red uptake assay. Vero E6 cells (uninfected) were incubated for 4 days in the presence of different concentrations of test-item, or with vehicle alone (medium only). For each data point the individual raw absorbance is shown (A540). Lower table shows raw data values for the vehicle alone, GS-441524 and CQ controls, and the cytotoxic agent (DMSO at 10%).

TABLE 6

| Viability of Uninfected Vero E6 Cells (A540) | | | | | | | | |
|---|---|---|---|---|---|---|---|---|
| | Conc. (μg/mL) | | | | | | | |
| | 1,250 | 417 | 139 | 46 | 15 | 5.1 | 1.7 | 0.57 |
| PPCM Na | 1.142 | 1.268 | 1.476 | 1.370 | 1.514 | 1.228 | 1.475 | 1.714 |
| Salt | 1.238 | 1.196 | 1.193 | 1.351 | 1.445 | 1.677 | 1.668 | 1.409 |
| | 1.094 | 1.189 | 1.238 | 1.474 | 1.337 | 1.372 | 1.562 | 1.719 |

TABLE 6-continued

| Viability of Uninfected Vero E6 Cells (A540) | | |
|---|---|---|
| Controls | Viability (A540) | |
| No Cells (Background) | 0.077 | |
| Medium Only | 1.533 | 1.746 |
| | 1.697 | 1.651 |
| | 1.440 | 1.537 |
| GS-441524 (10 μM) | 1.616 | 1.479 |
| GS-441524 (1 μM) | 1.404 | 1.753 |
| CQ (5 μM) | 1.206 | 1.262 |
| DMSO (10%) | 0.074 | 0.073 |
| PBS (12.5%) | 1.282 | 1.641 |

Table 7, shown below, illustrates viability of Vero E6 cells determined by the neutral red uptake assay (percentage values). Values indicate the percent viability remaining in uninfected Vero E6 after a 4-day treatment with test-items. Values are shown as percentage of the viability observed in samples incubated with vehicle alone (medium only). Data represent the mean and standard deviation of triplicates. Vehicle values were derived from six replicates. Bottom table show the percentage viability observed in cells treated with tissue culture medium in the absence of test-item, or with control inhibitors GS-441524 and CQ, or the cytotoxic agent (DMSO at 10%).

TABLE 7

| Viability of Uninfected Vero E6 Cells (% Vehicle) | | | | | | | | |
|---|---|---|---|---|---|---|---|---|
| | Conc. (μg/mL) | | | | | | | |
| | 1,250 | 417 | 139 | 46 | 15 | 5.1 | 1.7 | 0.57 |
| PPCM Na Salt | 70.9 ± 4.8 | 74.9 ± 2.9 | 80.4 ± 10.0 | 86.7 ± 4.3 | 88.9 ± 5.9 | 88.5 ± 15.0 | 97.9 ± 6.3 | 100.9 ± 11.7 |

| Viability of Uninfected Vero E6 Cells (% Vehicle) | |
|---|---|
| Controls | Viability (A540) |
| No Cells (Background) | 0.0 |
| Medium Only | 100.0 ± 7.6 |
| GS-441524 (10 μM) | 96.5 ± 6.4 |
| GS-441524 (1 μM) | 98.5 ± 16.2 |
| CQ (5 μM) | 75.9 ± 2.6 |
| DMSO (10%) | −0.2 ± 0.0 |
| PBS (12.5%) | 90.9 ± 16.7 |

Table 8, shown below, illustrates IAV infectivity assay (A490). Individual viability values (as quantified by absorbance measured at 490 nm) are shown for each test condition. Infected cells display increased absorbance levels. Quadruplicate A540 values are shown for each test-item concentration. All samples were infected except those indicated as "mock". Samples treated with baloxavir (BLX) (0.2 µM) and with PBS (12.5%) are also shown. Varying concentrations of BLX were also evaluated. Test-item concentrations are shown in µg/mL and BLX in nM.

TABLE 8

IVA Infectivity in A549 Cells (Absorbance 490 nm)

| | Conc. (µg/mL) | | | | | | | | | | | | |
|---|---|---|---|---|---|---|---|---|---|---|---|---|---|
| | 1,250 | 417 | 139 | 46 | 15 | 5.1 | 1.7 | 0.57 | Vehicle | Vehicle (12.5% PBS) | BLX (0.2 µM) | Mock | No Cells |
| PPCM | 0.463 | 0.671 | 1.062 | 1.167 | 1.148 | 1.128 | 1.158 | 1.188 | 1.138 | 1.172 | 0.391 | 0.336 | 0.210 |
| Na Salt | 0.418 | 0.640 | 1.002 | 1.092 | 1.013 | 1.055 | 1.069 | 1.069 | 1.022 | 1.233 | 0.374 | 0.346 | 0.263 |
| | 0.452 | 0.565 | 0.880 | 1.025 | 1.056 | 1.007 | 1.089 | 1.088 | 1.059 | 1.157 | 0.383 | 0.325 | |
| | 0.451 | 0.649 | 1.009 | 1.104 | 1.102 | 1.068 | 1.123 | 1.136 | 1.104 | 1.188 | | 0.337 | |

| | Conc. (nM) | | | | | | | | |
|---|---|---|---|---|---|---|---|---|---|
| | 1,000 | 200 | 40 | 8.0 | 1.6 | 0.32 | 0.06 | 0.01 | 1.136 |
| Baloxavir | 0.419 | 0.382 | 0.379 | 0.383 | 0.471 | 0.828 | 1.000 | 1.064 | 1.142 |

Table 9, shown below, illustrates IAV infectivity assay (percentage values). Data represent infectivity as a percentage of values obtained from infected cells treated with vehicle alone (medium only). The average of quadruplicate data points with the standard deviation (s.d) are shown for test-item. All samples shown below were infected except those indicated as "mock". Some samples are treated with the control antiviral, baloxavir, (BLX). Test-item concentrations are shown in micrograms per mL and control in nanomolar. Data shown for test-item represent the average and standard deviation of quadruplicates. For uninfected cells ("mock") and "vehicle", the standard deviation was derived from four or six replicates, respectively.

TABLE 9

IAV Infectivity in A549 Cells (% Vehicle)

| | Conc. (µg/mL) | | | | | | | | | | | |
|---|---|---|---|---|---|---|---|---|---|---|---|---|
| | 1,250 | 417 | 139 | 46 | 15 | 5.1 | 1.7 | 0.57 | Vehicle | Vehicle (12.5% PBS) | BLX (0.2 µM) | Mock |
| PPCM Na Salt | 14.3 ± 2.6 | 38.6 ± 6.0 | 85.3 ± 10.1 | 99.6 ± 7.6 | 97.4 ± 7.6 | 95.3 ± 6.5 | 101.2 ± 5.1z | 102.6 ± 7.0 | 100.0 ± 6.5 | 111.4 ± 4.3 | 6.0 ± 1.1 | 0.0 ± 1.1 |

| | Conc. (nM) | | | | | | | |
|---|---|---|---|---|---|---|---|---|
| | 1,000 | 200 | 40 | 8.0 | 1.6 | 0.32 | 0.06 | 0.01 |
| Baloxavir | 10.8 | 6.0 | 5.6 | 6.1 | 17.7 | 64.4 | 86.9 | 95.3 |

Table 10, shown below, illustrates viability of A549 cells in the presence of test-items as determined by the XTT assay (A490). Individual replicate viability values (as quantified by absorbance measured at 490 nm) are shown for each test condition. For each data point, the individual raw datum is shown. Lower table shows raw data values for the control samples.

TABLE 10

Viability in A549 Cells (A490)

| | Conc. (µg/mL) | | | | | | | |
|---|---|---|---|---|---|---|---|---|
| | 1,250 | 417 | 139 | 46 | 15 | 5.1 | 1.7 | 0.57 |
| PPCM | 0.858 | 0.910 | 0.926 | 0.926 | 0.983 | 0.970 | 0.999 | 0.942 |
| Na Salt | 0.843 | 0.787 | 0.897 | 0.911 | 0.922 | 0.983 | 0.933 | 0.916 |
| | 0.884 | 0.872 | 0.852 | 0.872 | 0.917 | 0.910 | 0.881 | 0.895 |
| | 0.831 | 0.843 | 0.901 | 0.913 | 0.940 | 0.926 | 0.934 | 0.989 |

TABLE 10-continued

| Controls | Viability (A490) | |
|---|---|---|
| No Cells (Background) | 0.088 | 0.083 |
| | 0.911 | 0.944 |
| Medium Only | 0.980 | 0.963 |
| | 1.001 | 0.962 |
| | 0.949 | 0.953 |
| Vehicle (12.5% PBS) | 0.920 | 0.932 |
| | 0.922 | 0.952 |
| BLX (0.2 µM) | 0.945 | 0.989 |
| | 0.976 | 0.990 |
| Emetine (10 µM) | 0.236 | 0.179 |

Table 11, shown below, illustrates viability of A549 cells determined by the XTT assay (percentage values). Data represent viability as a percentage of values obtained from uninfected wells treated with vehicle (medium only). The average value obtained from the background wells was subtracted from all raw values before normalization to vehicle. Mean of quadruplicates with their standard deviation are shown for the test-item, BLX, and vehicle 12.5%, or from six replicates for vehicle alone (medium only).

TABLE 11

| Viability in A549 Cells (% Vehicle) | | | | | | | | |
|---|---|---|---|---|---|---|---|---|
| | Conc. (μg/mL) | | | | | | | |
| | 1,250 | 417 | 139 | 46 | 15 | 5.1 | 1.7 | 0.57 |
| PPCM Na Salt | 88.1 ± 2.6 | 88.0 ± 6.0 | 92.7 ± 3.6 | 94.0 ± 2.7 | 98.0 ± 3.4 | 98.8 ± 3.9 | 97.6 ± 5.5 | 97.4 ± 4.6 |

| Viability in A549 cells (% Vehicle) | |
|---|---|
| Controls | Viability (A490) |
| No Cells (Background) | 0.0 ± 0.4 |
| Medium Only | 100.0 ± 3.0 |
| Vehicle (12.5% PBS) | 97.0 ± 1.7 |
| BLX (0.2 μM) | 102.0 ± 2.4 |
| Emetine (10 μM) | 14.0 ± 4.6 |

In view of the aforementioned, in some embodiments, the present disclosure pertains to compositions containing a polymer of mandelic acid that can be in the form of an aqueous solution that can be applied to the skin, nose, hands, hair, and eyes, thereby providing an extra layer of protection from infection both internally and externally. In some embodiments, the polymer of mandelic acid is PPCM. In some embodiments, the compositions of the present disclosure can include additional excipients that are used in skin, eye, and nasal compositions. In some embodiments, the present disclosure pertains to methods of internal and external use of various skin, nasal, and eye aqueous compositions to enhance protection from viral and bacterial infection. In some embodiments, the compositions of the present disclosure include a drug product having an aqueous dosage form containing a polymer of mandelic acid that can be delivered using various dosing devices, including, but not limited to, dosing devices for skin, dosing devices for eyes, dosing devices for nasal passages, and combinations thereof. In some embodiments, the dosing device can include, without limitation, lotion bottles, pump bottles, dispenser spray bottles, dry powder inhalers, metered dose inhalers, nebulizers, gauze-tipped applicators, and combinations of the same and like.

In some embodiments, the present disclosure pertains to an aqueous composition that includes a synthesized active polymer pharmaceutical. In some embodiments, the aqueous composition is in the form of an aqueous nasal preparation in which the active polymer pharmaceutical has an average molecular weight (Mw) less than 10,000 Daltons and is soluble in water. In some embodiments, the active polymer pharmaceutical includes a condensation polymer of mandelic acid with a sulfur content (wt. %)<0.1. In some embodiments, the condensation polymer of mandelic acid is PPCM. In some embodiments, the active polymer pharmaceutical includes a condensation polymer synthesized using only water or ethanol as solvents. In some embodiments, the present disclosure pertains to an aqueous composition that is muccoadhesive. In some embodiments, the aqueous composition further includes excipients found in skin, nasal, or eye compositions.

In some embodiments, the compositions of the present disclosure prevent primary viral infections via skin, punctured skin, eyes, the respiratory tract, or combinations thereof. In some embodiments, the viral infections are viral infections from the viral family including, but not limited to, Adenoviridae, Picornaviridae, Togaviridae, Orthomyxoviridae, Paramyxoviridae, Filoviridae, Coronavirus, Poxviridae, Flaviviridae, Hepadnaviridae, Herpesviridae, Papillomaviridae, and combinations thereof. In some embodiments, the viral infections include, without limitation, adenoviruses, rhinovirus, poliovirus, rubella virus, influenza (A, B, and C), measles, mumps, respiratory syncytial infection (RSI), Ebola virus, coronavirus, severe acute respiratory syndrome (SARS), and Coronavirus disease 2019 (COVID-19), Smallpox, Yellow Fever, Dengue Fever, West Nile Viruses, Zika Virus, Hepatitis C, Hepatitis B, Herpes Simplex Virus (HSV-1 and HSV-2), Human Papillomavirus (HPV), and combinations thereof. In some embodiments, the viral infections are sexually transmitted diseases. In some embodiments, the viral infections are airborne pathogens. Newly discovered viruses not classified in the above-mentioned groups are also envisioned.

In some embodiments, the compositions of the present disclosure prevents bacterial infections via skin, punctured skin, eyes, the respiratory tract, or combinations thereof. In some embodiments, the bacterial infections are bacterial infections from bacteria including, but not limited to, *Bordetella pertussis, Mycoplasma pneumoniae, Chlamydia pneumoniae, Klebsiella pneumoniae, Haemophilus influenzae, Pseudomonas aeruginosa, Pseudomonas pseudomallei, Actinomyces israelii, Legionella parisiensis, Legionella pneumophila, Cardiobacterium, Alkaligenes, Yersinia pestis, Pseudomonas cepacia, Pseudomonas maillei, Enterobacter cloacae, Enterococcus, Neisseria meningitidis, Streptococcus faecalis, Streptococcus pyogenes, Mycobacterium kansasii, Mycobacterium tuberculosis, Streptococcus pneumoniae, Staphylococcus aureus, Staphylococcus epidermis, Corynebacteria diphtheria, Clostridium tetani, Haemophilus parainfluenzae, Moraxella lacunata, Bacillus anthracis, Mycobacterium avium, Mycobacterium intracellulare, Acinetobacter, Moraxella catarrhalis, Serratia marcescens, Saccharomonospora viridis, Neisseria gonorrhoeae, Treponema pallidum*, and combinations thereof. Newly discovered bacteria not classifiable to the above-mentioned groups are also envisioned. In some embodiments, the bacterial infection includes, without limitation, whooping cough, pneumonia, bronchitis, meningitis, actinomycosis, pneumonia, Legionnaires' disease, pontiac fever, opportunistic infections, pneumonic plague, non-respiratory infections, meningitis, scarlet fever, pharyngitis, cavitary pulmonary, tuberculosis, pneumonia, otitis media, diptheria, anthrax, opportunistic infections, farmer's lung, gonorrhea, syphilis, sexually transmitted diseases, and combinations thereof. In some embodiments, the bacterial infections are contagious, non-contagious, endogenous, and combinations thereof. In some embodiments, the bacterial infections are bacterial infections are transmitted via a route including, without limitation, via humans, rodents, cattle, the environment, agriculture, and combinations thereof.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A method to minimize infectivity and replication of a pathogen or reduce inflammation caused by an infection, the method comprising:

administering a composition to a subject, wherein the administering comprises a mechanism selected from the group consisting of nasal administration and nasal spray administration; and wherein the composition is an aqueous solution of a sodium salt of polyphenylene carboxymethylene (PPCM); and further wherein the infection is caused by a virus selected from the group consisting of adenoviruses, rhinovirus, influenza A, influenza B, influenza C, measles, mumps, respiratory syncytial infection (RSI), Ebola virus, coronavirus, severe acute respiratory syndrome (SARS), and Coronavirus disease 2019 (COVID-19).

2. The method of claim 1, further comprising at least one of:

binding, by the composition, to a virus associated with the infection to thereby inhibit replication of the virus; and reducing, by the composition, inflammation related to the infection.

3. The method of claim 1, wherein the PPCM comprises a sulfur content less than 0.1 wt. %.

4. The method of claim 1, wherein the administering comprises internal administration to the subject; and wherein the administering comprises distributing the composition to an internal region of the subject selected from the group consisting of a lung, a tracheobronchial airway, a pulmonary airway, a nasal passage, a throat, a trachea, an extrathoracic airway, a respiratory tract, pharyngeal areas, laryngeal airways and oral.

5. The method of claim 1, wherein the composition has an average molecular weight of less than 10,000 Daltons.

6. The method of claim 1, wherein the composition is in a form selected from the group consisting of an aqueous solution, a gel, a lotion, a cream, an aerosol, and a nasal aqueous solution.

* * * * *